(12) United States Patent
Fu et al.

(10) Patent No.: US 10,709,611 B2
(45) Date of Patent: Jul. 14, 2020

(54) SYSTEMS AND METHODS FOR LENTICULAR LASER INCISION

(71) Applicant: AMO Development, LLC, Santa Ana, CA (US)

(72) Inventors: Hong Fu, Pleasanton, CA (US); Alireza Malek Tabrizi, Fremont, CA (US)

(73) Assignee: AMO Development, LLC, Santa Ana, CA (US)

( * ) Notice: Subject to any disclaimer, the term of this patent is extended or adjusted under 35 U.S.C. 154(b) by 141 days.

(21) Appl. No.: 16/109,654

(22) Filed: Aug. 22, 2018

(65) Prior Publication Data
US 2019/0060122 A1 Feb. 28, 2019

Related U.S. Application Data

(63) Continuation-in-part of application No. 14/865,396, filed on Sep. 25, 2015, now Pat. No. 10,369,052.
(Continued)

(51) Int. Cl.
| | | |
|---|---|---|
| A61F 9/008 | (2006.01) | |
| A61B 3/107 | (2006.01) | |
| A61B 3/00 | (2006.01) | |

(52) U.S. Cl.
CPC ........ *A61F 9/00827* (2013.01); *A61B 3/0008* (2013.01); *A61B 3/107* (2013.01);
(Continued)

(58) Field of Classification Search
CPC .................. A61F 9/00827; A61F 2009/00872
See application file for complete search history.

(56) References Cited

U.S. PATENT DOCUMENTS

| 4,665,913 A | 5/1987 | L'Esperance, Jr. |
| 4,669,466 A | 6/1987 | L'Esperance |

(Continued)

FOREIGN PATENT DOCUMENTS

| DE | 102006053119 A1 | 5/2008 |
| WO | 04032810 A2 | 4/2004 |
| WO | 2013053366 A1 | 4/2013 |

OTHER PUBLICATIONS

International Search Report and Written Opinion for Application No. PCT/US2015/052199, dated Dec. 9, 2015, 16 pages.

*Primary Examiner* — Gary Jackson
*Assistant Examiner* — Zahed Kabir
(74) *Attorney, Agent, or Firm* — Johnson & Johnson Surgical Vision, Inc.

(57) ABSTRACT

Embodiments of this invention generally relate to ophthalmic laser procedures and, more particularly, to systems and methods for lenticular laser incision. In an embodiment, an ophthalmic surgical laser system comprises a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top lenticular incision and a bottom lenticular incision of a lens in the subject's eye, where each of the top and bottom lenticular incision includes a center spherical portion and an edge transition portion that is not located on the same spherical surface as the spherical portion but has a steeper shape.

13 Claims, 19 Drawing Sheets

Related U.S. Application Data

(60) Provisional application No. 62/183,653, filed on Jun. 23, 2015, provisional application No. 62/055,437, filed on Sep. 25, 2014.

(52) U.S. Cl.
CPC .. *A61F 9/00834* (2013.01); *A61F 2009/0088* (2013.01); *A61F 2009/00848* (2013.01); *A61F 2009/00872* (2013.01); *A61F 2009/00887* (2013.01); *A61F 2009/00897* (2013.01)

(56) References Cited

U.S. PATENT DOCUMENTS

| | | |
|---|---|---|
| 4,732,148 A | 3/1988 | L'Esperance, Jr. |
| 4,764,930 A | 8/1988 | Bille et al. |
| 4,770,172 A | 9/1988 | L'Esperance, Jr. |
| 4,773,414 A | 9/1988 | L'Esperance, Jr. |
| 5,108,388 A | 4/1992 | Trokel |
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,646,791 A | 7/1997 | Glockler |
| 5,993,438 A | 11/1999 | Juhasz et al. |
| 6,110,166 A | 8/2000 | Juhasz |
| 6,210,401 B1 | 4/2001 | Lai |
| 6,315,413 B1 | 11/2001 | Shimmick et al. |
| 8,260,024 B2 | 9/2012 | Farrer et al. |
| 8,394,084 B2 | 3/2013 | Blumenkranz et al. |
| 8,403,921 B2 | 3/2013 | Blumenkranz et al. |
| 8,690,862 B2 | 4/2014 | Palanker et al. |
| 8,709,001 B2 | 4/2014 | Blumenkranz et al. |
| 2010/0318073 A1* | 12/2010 | Vogler .................. A61F 9/008 606/4 |
| 2010/0331831 A1* | 12/2010 | Bischoff ................ A61F 9/008 606/5 |
| 2011/0172649 A1 | 7/2011 | Schuele |
| 2012/0016351 A1* | 1/2012 | Stobrawa ............... A61F 9/008 606/5 |
| 2012/0083667 A1 | 4/2012 | Isogai et al. |
| 2012/0083775 A1* | 4/2012 | Donitzky ............ A61F 9/00804 606/5 |
| 2012/0310223 A1 | 12/2012 | Knox et al. |
| 2012/0310224 A1 | 12/2012 | Miyagi |
| 2013/0281992 A1 | 10/2013 | Seiler et al. |
| 2013/0338648 A1 | 12/2013 | Hanebuchi et al. |
| 2014/0104576 A1 | 4/2014 | Bor et al. |
| 2014/0350533 A1 | 11/2014 | Horvath et al. |
| 2014/0364840 A1 | 12/2014 | Donitzky et al. |
| 2015/0051591 A1 | 2/2015 | Hanebuchi et al. |
| 2015/0297311 A1 | 10/2015 | Tesar et al. |
| 2016/0089270 A1 | 3/2016 | Fu |
| 2018/0193196 A1 | 7/2018 | Bergt et al. |

\* cited by examiner

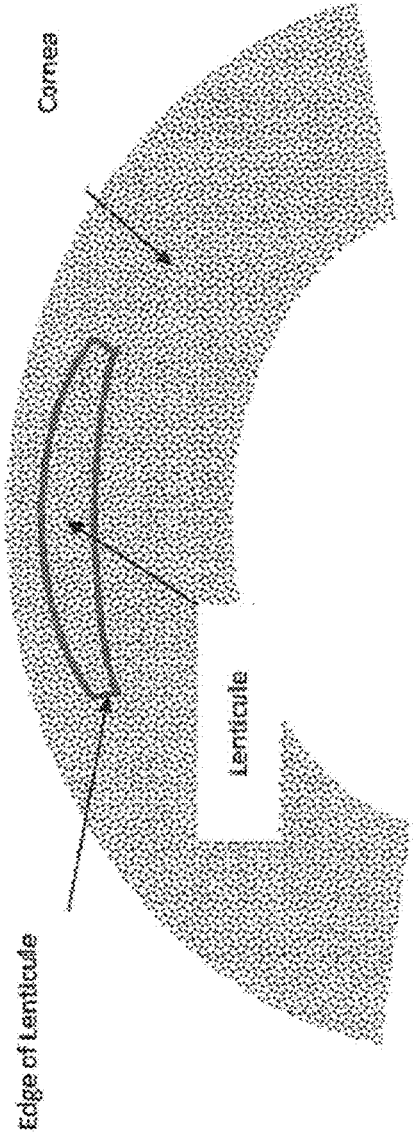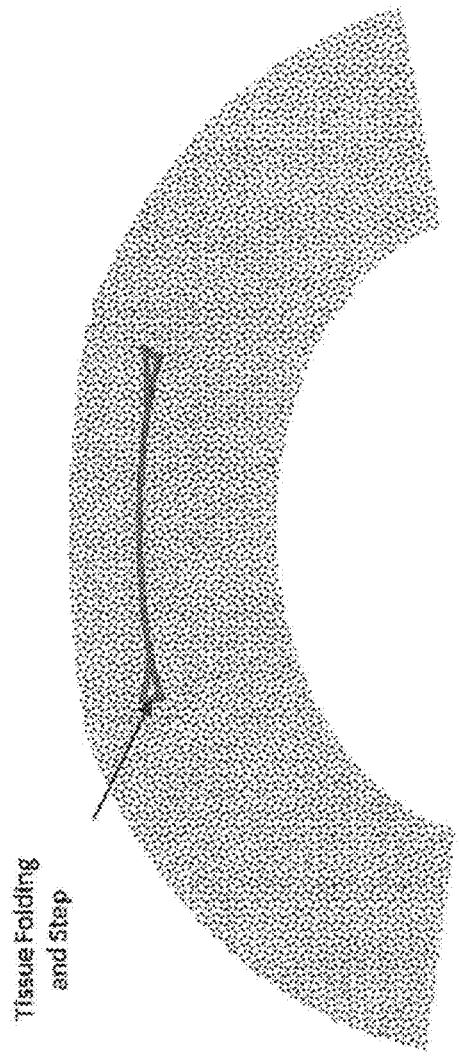

SYSTEMS AND METHODS FOR LENTICULAR LASER INCISION

RELATED APPLICATIONS

This application is a continuation-in-part under 35 U.S.C. § 120 of U.S. application Ser. No. 14/865,396, filed Sep. 25, 2015, which is a non-provisional application and claims the benefit under 35 U.S.C. § 119(e) of U.S. Provisional Application Ser. No. 62/055,437, filed Sep. 25, 2014 and 62/183,653, filed Jun. 23, 2015. All of the above mentioned applications are incorporated herein in their entirety as if fully set forth.

BACKGROUND OF THE INVENTION

Field of the Invention

Embodiments of this invention relate generally to laser-assisted ophthalmic procedures, and more particularly, to systems and methods for lenticular incisions in the cornea.

Description of Related Art

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures. The reason eye surgeons prefer a surgical laser beam over manual tools like microkeratomes and forceps is that the laser beam can be focused precisely on extremely small amounts of ocular tissue, thereby enhancing accuracy and reliability of the procedure. These in turn enable better wound healing and recovery following surgery.

Hyperopia (far-sightedness) is a visual impairment where light entering the eye does not focus at the retina to produce a sharp image as desired, but rather focuses at a location behind the retina such that a patient sees a blurred disc. The basic principle to treating hyperopia is to add positive focusing power to the cornea. For instance, a hyperopic eye can be treated by placing a convex lens in front of the eye to add a positive focusing power to the eye. After correction, light passing through the convex lens and into the eye focuses at the retina to form a sharp image.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm. Examples of laser systems that provide ultra-short pulsed laser beams include the Abbott Medical Optics iFS Advanced Femtosecond Laser, the IntraLase FS Laser, and OptiMedica's Catalys Precision Laser System.

Prior surgical approaches for reshaping the cornea include laser assisted in situ keratomileusis (hereinafter "LASIK"), photorefractive keratectomy (hereinafter "PRK") and Small Incision Lens Extraction (hereinafter "SmILE").

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like.

It is known that if part of the cornea is removed, the pressure exerted on the cornea by the aqueous humor in the anterior chamber of the eye will act to close the void created in the cornea, resulting in a reshaped cornea. By properly selecting the size, shape and location of a corneal void, one can obtain the desired shape, and hence, the desired optical properties of the cornea.

In current laser surgery treatments that correct hyperopia using LASIK and PRK, positive focusing power is added to the cornea by steepening the curvature of the cornea, by for example, removing a ring-shaped stroma material from the cornea. In a LASIK procedure, a flap is first created, then lifted up for the ring-shaped stroma material to be removed or ablated away by an excimer laser. The center of the cornea is not removed while more outward portions of the cornea are removed. The flap is then put back into place. The cornea thus steepens due to the void created in the cornea. Common patterns that steepen the cornea include ring, tunnel and toric shapes. LASIK can typically correct hyperopia for up to 5 D (diopter). In a PRK procedure where no flap is created, the epithelium layer is first removed, and the ring-shaped stroma material is then removed by an excimer laser. The epithelium layer will grow back within a few days after the procedure.

Recently, surgeons have started using another surgical technique other than LASIK and PRK for refractive correction. Instead of ablating corneal tissue with an excimer laser following the creation of a corneal flap, the newer SmILE technique involves tissue removal with two femtosecond laser incisions that intersect to create a lenticule for extraction. Lenticular extractions can be performed either with or without the creation of a corneal flap. With the flapless procedure, a refractive lenticule is created in the intact portion of the anterior cornea and removed through a small incision.

In the SmILE procedure illustrated in FIG. 10, a femtolaser 110 is used to make a side cut 120, an upper surface cut 130 and a lower surface cut 140 that forms a cut lens 150. A tweezer, for example, is then used to extract the cut lens beneath the anterior surface of the cornea 160 through the side cut 120. Recently, SmILE has been applied to treat myopia by cutting and extracting a convex lens-shaped stroma material with a femtosecond laser. However, SmILE techniques have not been applied in treating hyperopia.

Furthermore, as shown in FIG. 1, conventional femtosecond laser surgery systems generate a curved dissection surface to make a lenticular incision by scanning a laser focus on the intended dissection surface through a XY-scanning device and a Z-scanning device. This method does not use the more advantageous "fast-scan-slow-sweep" scanning scheme with femtosecond lasers having high repetition rate ("rep rate"), for e.g., in the MHz range. Using the "fast-scan-slow-sweep" scanning scheme for a lenticular incision, however, will generate vertical "steps" and will require many vertical side cuts, resulting in a lenticular dissection surface that is not smooth.

Therefore, there is a need for improved systems and methods to generate corneal lenticular incisions for high repetition rate femtosecond lasers to correct hyperopia.

SUMMARY OF THE INVENTION

Hence, to obviate one or more problems due to limitations and disadvantages of the related art, this disclosure provides embodiments including an ophthalmic surgical laser system comprising a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top lenticular incision and a bottom lenticular incision of a lens on the subject's eye. The XY-scan device deflects the pulsed laser beam to form a scan line. The scan line is tangential to the parallels of latitude of the lens. The scan line is then moved along the meridians of longitude of the lens. The top lenticular incision is moved over the top surface of the lens through the apex of the top surface of the lens, and the bottom lenticular incision is moved over the bottom surface of the lens through the apex of bottom surface of the lens.

Other embodiments disclose an ophthalmic surgical laser system comprising a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top concave lenticular incision and a bottom concave lenticular incision of a lens on the subject's eye.

In one aspect, embodiments of the present invention provide an ophthalmic surgical laser system, which includes: a laser delivery system for delivering a pulsed laser beam to a target in a subject's eye; an XY-scan device to deflect the pulsed laser beam; a Z-scan device to modify a depth of a focus of the pulsed laser beam; and a controller configured to control the XY-scan device and the Z-scan device to form a top lenticular incision and a bottom lenticular incision of a lens in a cornea of the subject's eye, wherein the top lenticular incision has a top convex spherical portion at a center and a top edge transition portion that surrounds the top spherical portion, the top spherical portion being a part of a first sphere, the top edge transition portion being not a part of the first sphere and being located within a volume defined by the first sphere, the top lenticular incision being a smooth surface, wherein the bottom lenticular incision has a bottom convex spherical portion at a center and a bottom edge transition portion that surrounds the bottom spherical portion, the bottom spherical portion being a part of a second sphere, the bottom edge transition portion being not a part of the second sphere and being located within a volume defined by the second sphere, the bottom lenticular incision being a smooth surface, wherein the top and bottom edge transition portions are mirror symmetrical to each other with respect to a transverse center plane perpendicular to an optical axis of the eye, and wherein the top and bottom edge transition portions intersect each other at an intersection location and both extend beyond the intersection location.

In another aspect, embodiments of the present invention provide a method for creating a lenticular incision using an ophthalmic surgical laser system, the method including the steps of: generating a pulsed laser beam; delivering the pulsed laser beam to a target in a subject's eye; deflecting, by an XY-scan device, the pulsed laser beam; modifying, by a Z-scan device, a depth of a focus of the pulsed laser beam; and controlling, by a controller, the XY-scan device and the Z-scan device to form a top lenticular incision and a bottom lenticular incision of a lens in a cornea of the subject's eye, wherein the top lenticular incision has a top spherical portion at a center and a top edge transition portion that surrounds the top spherical portion, the top spherical portion being a part of a first sphere, the top edge transition portion being not a part of the first sphere and being located within a volume defined by the first sphere, the top lenticular incision being a smooth surface, wherein the bottom lenticular incision has a bottom spherical portion at a center and a bottom edge transition portion that surrounds the bottom spherical portion, the bottom spherical portion being a part of a second sphere, the bottom edge transition portion being not a part of the second sphere and being located within a volume defined by the second sphere, the bottom lenticular incision being a smooth surface, wherein the top and bottom edge transition portions are mirror symmetrical to each other with respect to a transverse center plane perpendicular to an optical axis of the eye, and wherein the top and bottom edge transition portions intersect each other at an intersection location and both extend beyond the intersection location.

In some embodiments, in a side cross-sectional view, the top edge transition portion is a part of an ellipse, and the bottom edge transition portion is a part of another ellipse.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals.

Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIGS. 17A and 17B illustrate a conventional Small Incision Lenticule Extraction procedure.

DETAILED DESCRIPTION OF PREFERRED EMBODIMENTS

Embodiments of this invention are generally directed to systems and methods for laser-assisted ophthalmic procedures, and more particularly, to systems and methods for lenticular laser incisions.

Figure 1:
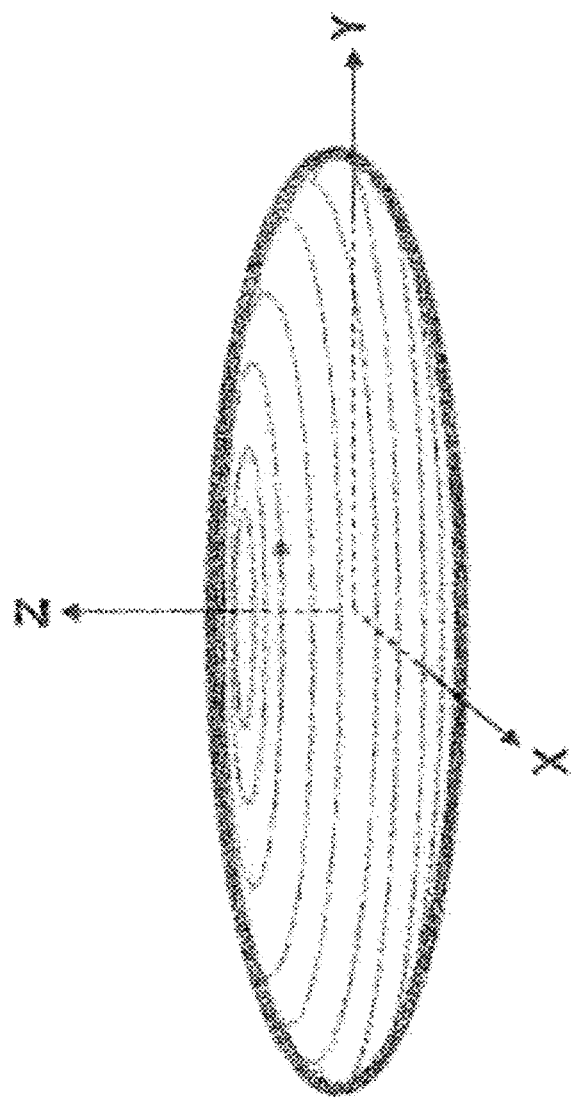
FIG. 1 illustrates a conventional lenticular cut via scanning a single focus spot.
Figure 2:
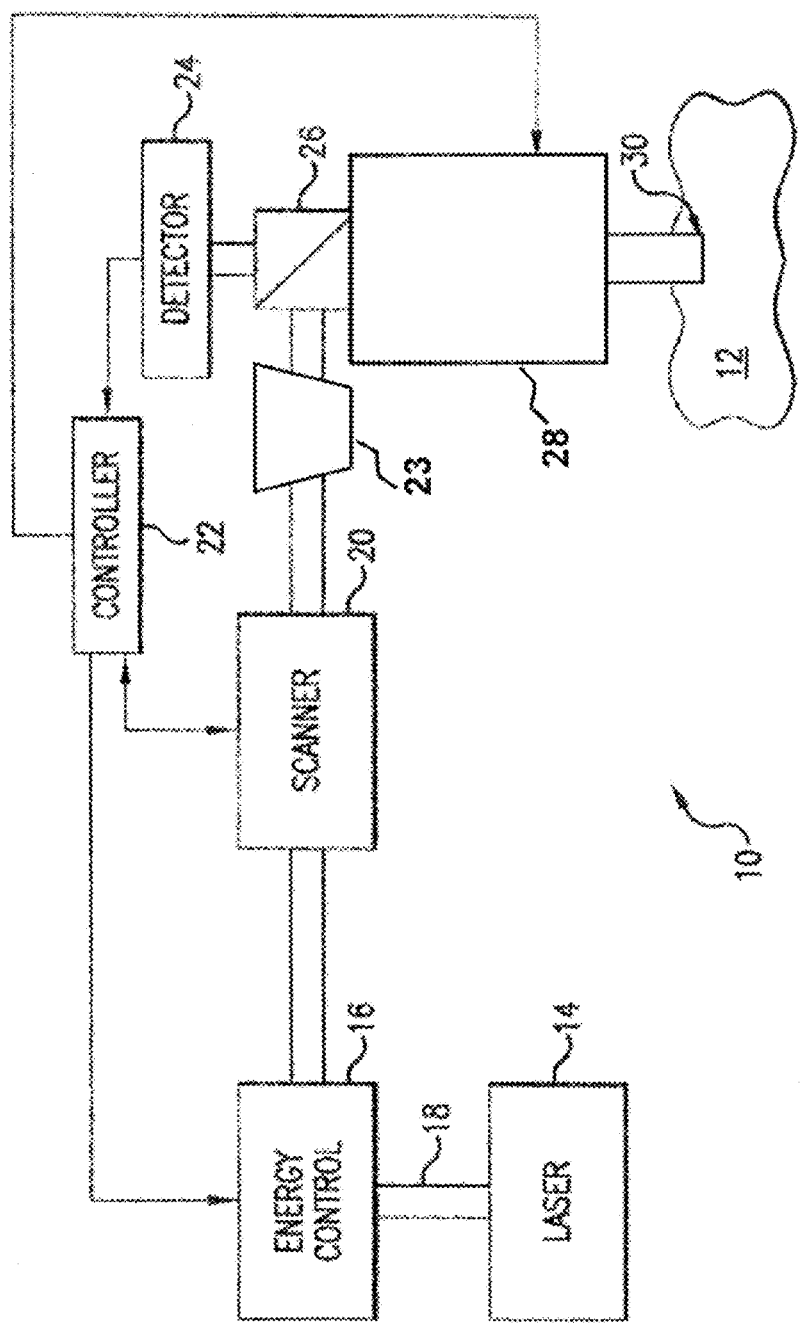
FIG. 2 is a simplified diagram of a surgical ophthalmic laser system according to an embodiment of the present invention.

Referring to the drawings, FIG. 2 shows a system 10 for making an incision in a material 12. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulse laser beam 18, a controller 22, a prism 23 (e.g., a Dove or Pechan prism, or the like), and an XY-scanner 28 for deflecting or directing the pulsed laser beam 18 from the laser 14 on or within the material 12. The controller 22, such as a processor operating suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to position encoder on the scanner 20, or the like. In an embodiment, the pattern of pulses may be summarized in machine readable data of tangible storage media in the form of a treatment table. The treatment table may be adjusted according to feedback input into the controller 22 from an automated image analysis system in response to feedback data provided from an ablation monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a sculpting or incision in response to the feedback, and may also modify the planned sculpting or incision based at least in part on the feedback. Measurement and imaging systems are further described in U.S. Pat. Nos. 6,315,413 and 8,260,024, the complete disclosures of which are incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam 18 toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam 18 toward the eye.

The laser system 10 is capable of generating the pulsed laser beam 18 with physical characteristics similar to those of the laser beams generated by a laser system disclosed in U.S. Pat. Nos. 4,764,930, 5,993,438, and U.S. patent application Ser. No. 12/987,069, filed Jan. 7, 2011, which are incorporated herein by reference.

Figure 3:
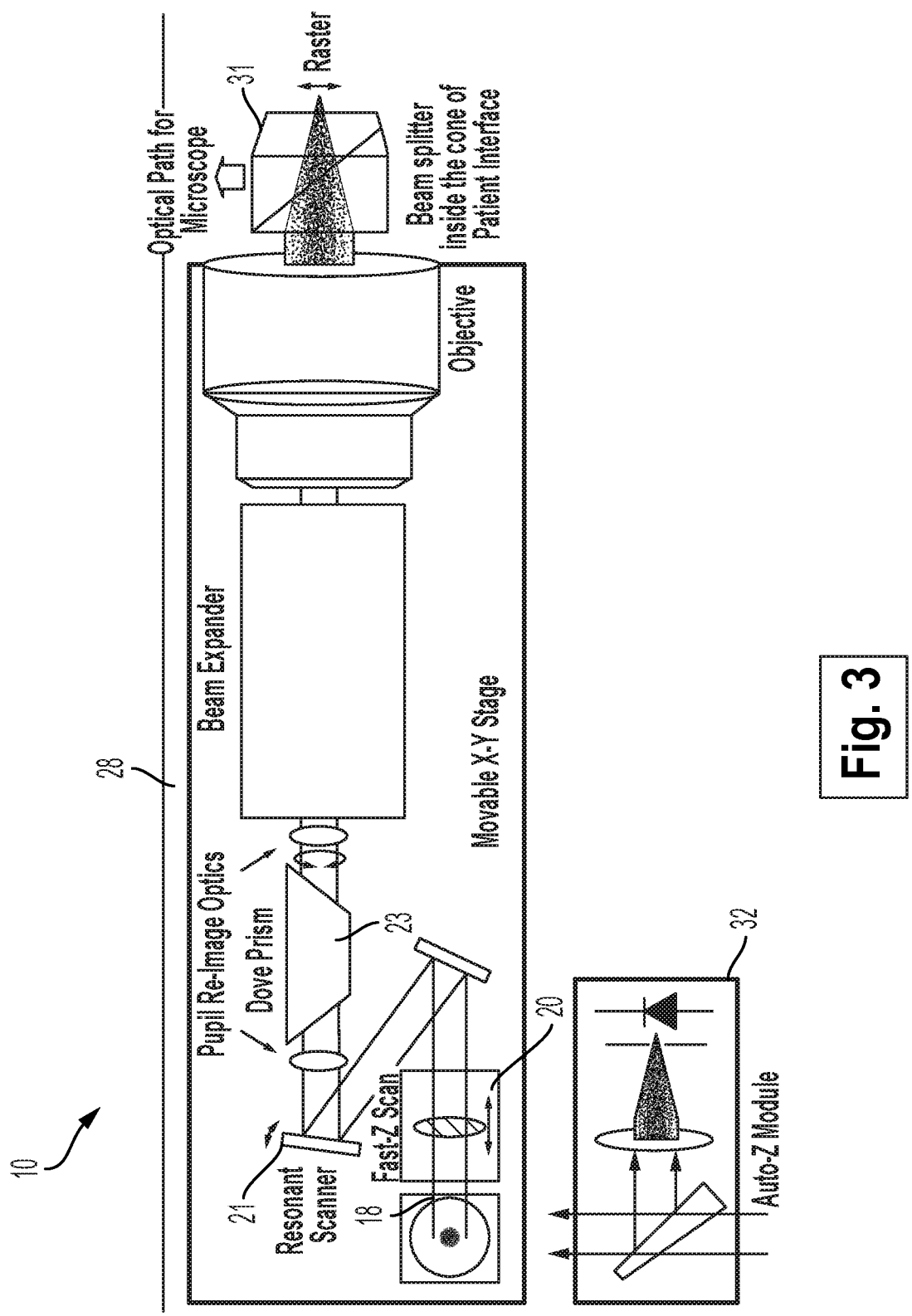
FIG. 3 is another simplified diagram of a surgical ophthalmic laser system according to an embodiment of the present invention.

FIG. 3 shows another exemplary diagram of the laser system 10. FIG. 3 shows a moveable XY-scanner (or XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 50-100 nJ range and pulse repetitive rates (or "rep rates") in the 5-20 MHz range. A fast-Z scanner 20 and a resonant scanner 21 direct the laser beam 18 to the prism 23. When used in an ophthalmic procedure, the system 10 also includes a patient interface 31 design that has a fixed cone nose and a portion that engages with the patient's eye. A beam splitter is placed inside the cone of the patient interface to allow the whole eye to be imaged via visualization optics. In one embodiment, the system 10 uses: optics with a 0.6 numerical aperture (NA) which would produce 1.1 μm Full Width at Half Maximum (FWHM) focus spot size; and a resonant scanner 21 that produces 1-2 mm scan line with the XY-scanner scanning the resonant scan line to a 10 mm field. The prism 23 rotates the resonant scan line in any direction on the XY plane. The fast-Z scanner 20 sets the incision depth and produces a side cut. The system 10 may also include an auto-Z module 32 to provide depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

Figure 4:
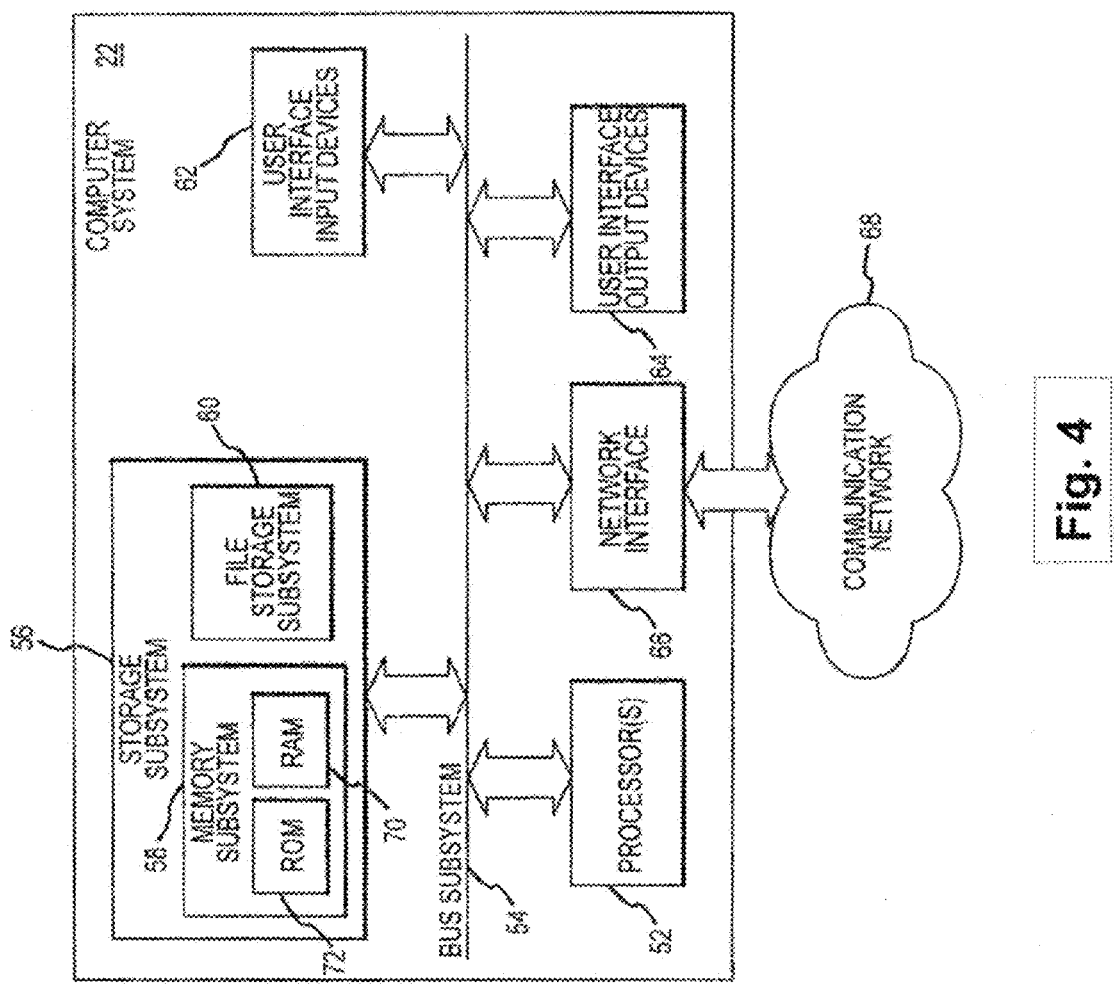
FIG. 4 is a simplified diagram of a controller of a surgical ophthalmic laser system according to an embodiment of the present invention.

FIG. 4 illustrates a simplified block diagram of an exemplary controller 22 that may be used by the laser system 10 according to an embodiment of this invention. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60. Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 4 is intended only as an example for purposes of illustrating only one embodiment of the present invention. Many other configurations of controller 22, having more or fewer components than those depicted in FIG. 4, are possible.

As should be understood by those of skill in the art, additional components and subsystems may be included with laser system 10. For example, spatial and/or temporal integrators may be included to control the distribution of energy within the laser beam, as described in U.S. Pat. No. 5,646,791, which is incorporated herein by reference. Ablation effluent evacuators/filters, aspirators, and other ancillary components of the surgical laser system are known in the art, and may be included in the system. In addition, an imaging device or system may be used to guide the laser beam. Further details of suitable components of subsystems that can be incorporated into an ophthalmic laser system for performing the procedures described here can be found in commonly-assigned U.S. Pat. Nos. 4,665,913, 4,669,466, 4,732,148, 4,770,172, 4,773,414, 5,207,668, 5,108,388, 5,219,343, 5,646,791, 5,163,934, 8,394,084, 8,403,921, 8,690,862, 8,709,001, U.S. application Ser. No. 12/987,069, filed Jan. 7, 2011, and U.S. application Ser. No. 13/798,457 filed Mar. 13, 2013, which are incorporated herein by reference.

In an embodiment, the laser surgery system 10 includes a femtosecond oscillator-based laser operating in the MHz range, for example, 10 MHz, for example, from several MHz to tens of MHz. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, i.e., moving the focal plane along an optical axis (e.g., the Z-axis), may be achieved by moving the focusing objective, or one or more lenses within the focusing objective, along the optical axis. It is noted that in many embodiments, the XY-scanner 28 deflects the pulse laser beam 18 to form a scan line.

Figure 5:
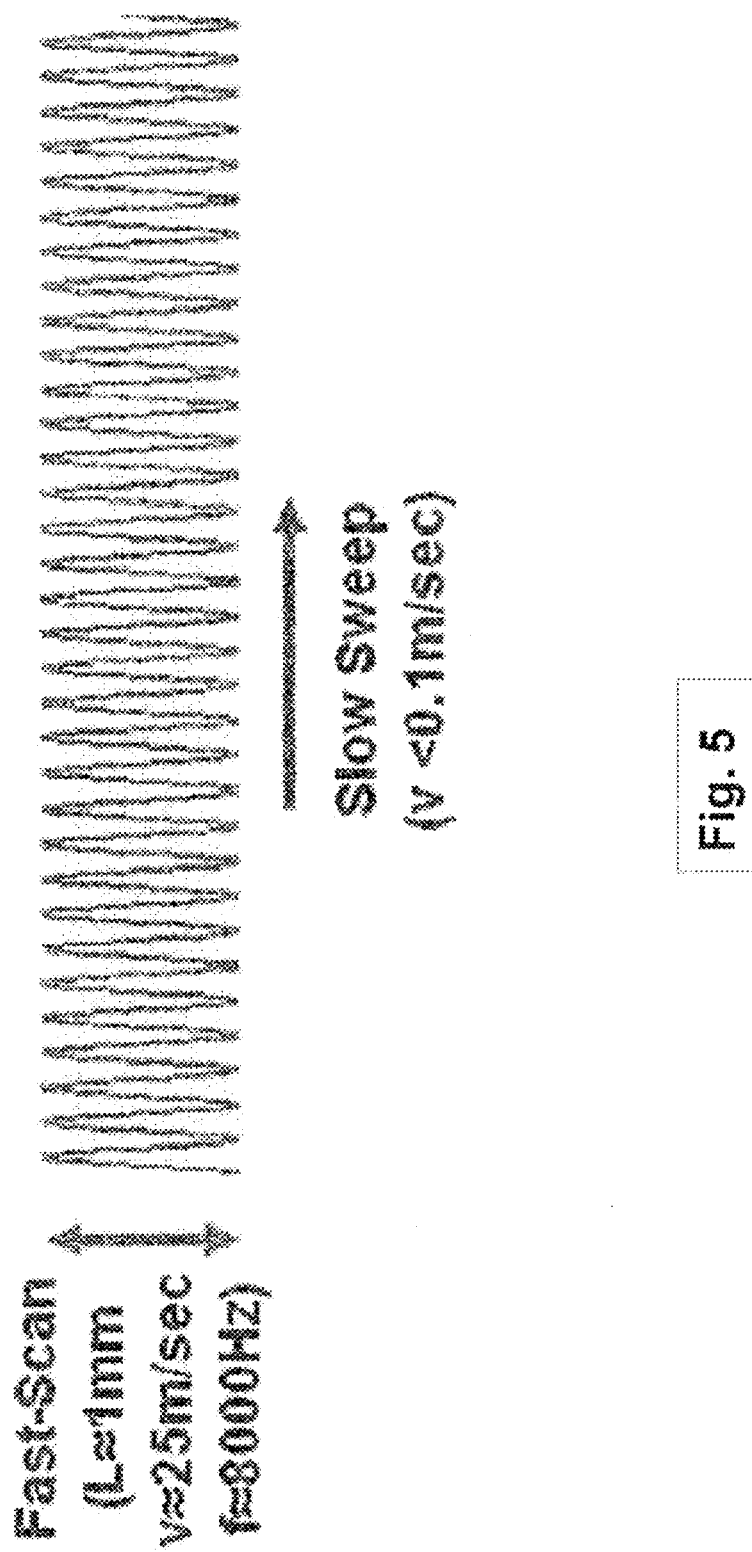
FIG. 5 illustrates an exemplary scanning of a surgical ophthalmic laser system according to an embodiment of the present invention.

In other embodiments, the beam scanning can be realized with a "fast-scan-slow-sweep" scanning scheme. The scheme consists of two scanning mechanisms: first, a high frequency fast scanner is used to produce a short, fast scan line (e.g., a resonant scanner 21 of FIG. 3); second, the fast scan line is slowly swept by much slower X, Y, and Z scan mechanisms. FIG. 5 illustrates a scanning example of a laser system 10 using an 8 kHz resonant scanner 21 to produce a scan line of about 1 mm and a scan speed of about 25 m/sec, and X, Y, and Z scan mechanisms with the scan speed smaller than 0.1 m/sec. The fast scan line may be perpendicular to the optical beam propagation direction, i.e., it is always parallel to the XY plane. The trajectory of the slow sweep can be any three dimensional curve drawn by the X, Y, and Z scanning devices (e.g., XY-scanner 28 and Z-scanner 20). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 6:
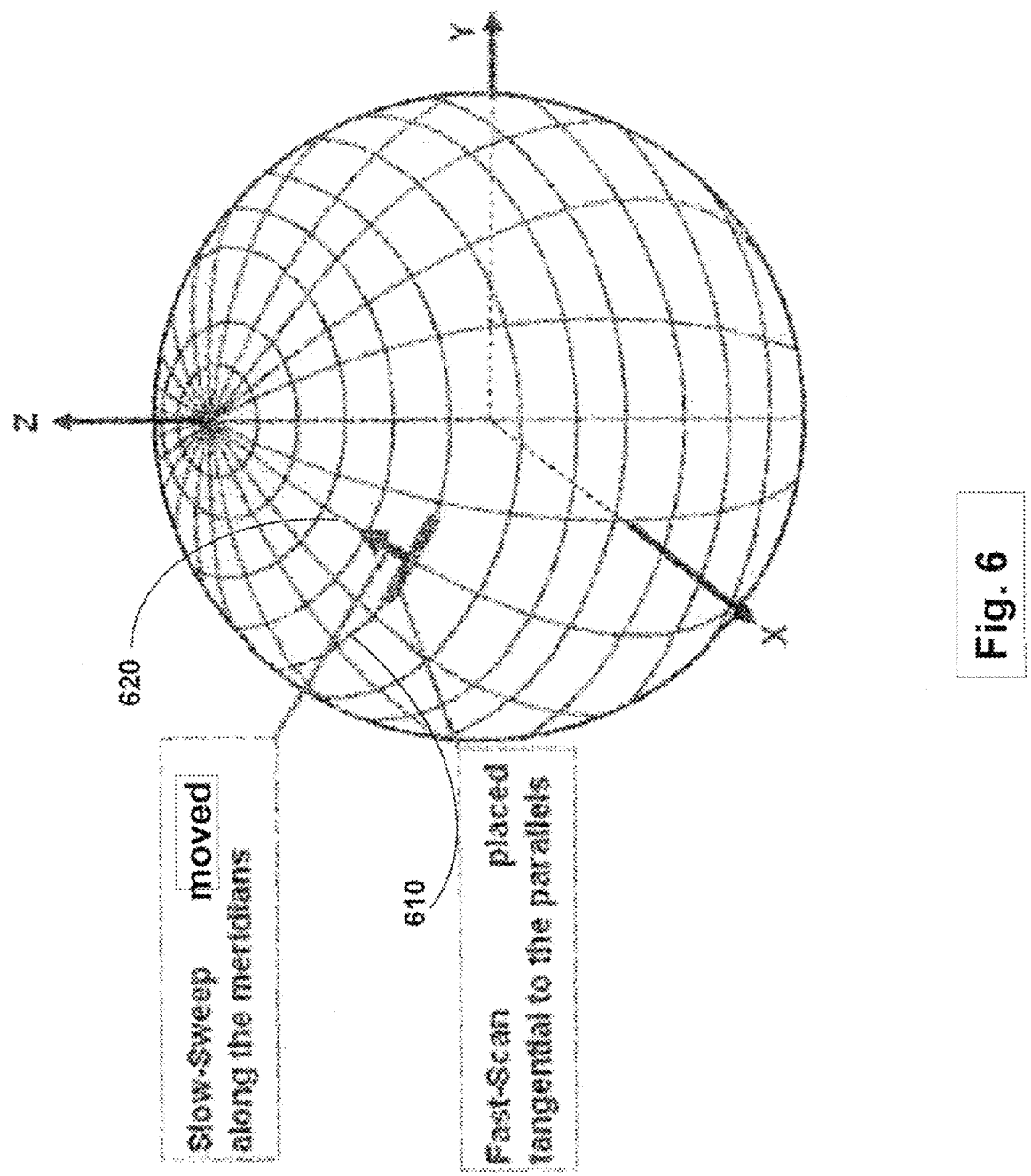
FIG. 6 illustrates an exemplary lenticular incision using a fast-scan-slow-sweep scheme of a surgical ophthalmic laser system according to an embodiment of the present invention.

In another embodiment shown in FIG. 6, the laser system 10 creates a smooth lenticular cut using the "fast-scan-slow-sweep" scanning scheme under a preferred procedure. First, in a three dimensional lenticular cut, the fast scan line is preferably placed tangential to the parallels of latitude 610. For example, in the miniaturized flap maker laser system 10 of FIG. 3, this can be realized by adjusting a prism 23 to the corresponding orientations via software, e.g., via the controller 22. Second, the slow sweep trajectory preferably moves along the meridians of longitude 620. For example, in the miniaturized flap maker system of FIG. 3, this can be done by coordinating the XY scanner 28, and the Fast-Z scanner 20 via the software, e.g., via the controller 22. The procedure starts with the scan line being parallel to the XY plane, and sweeps through the apex of the lens, following the curvature with the largest diameter (see also FIG. 8). With this preferred procedure, there are no vertical "steps" in the dissection, and vertical side cuts are eliminated. As will be analyzed herein below, the deviations between the laser focus locations and the intended spherical surface dissections are also minimized.

Figure 7:
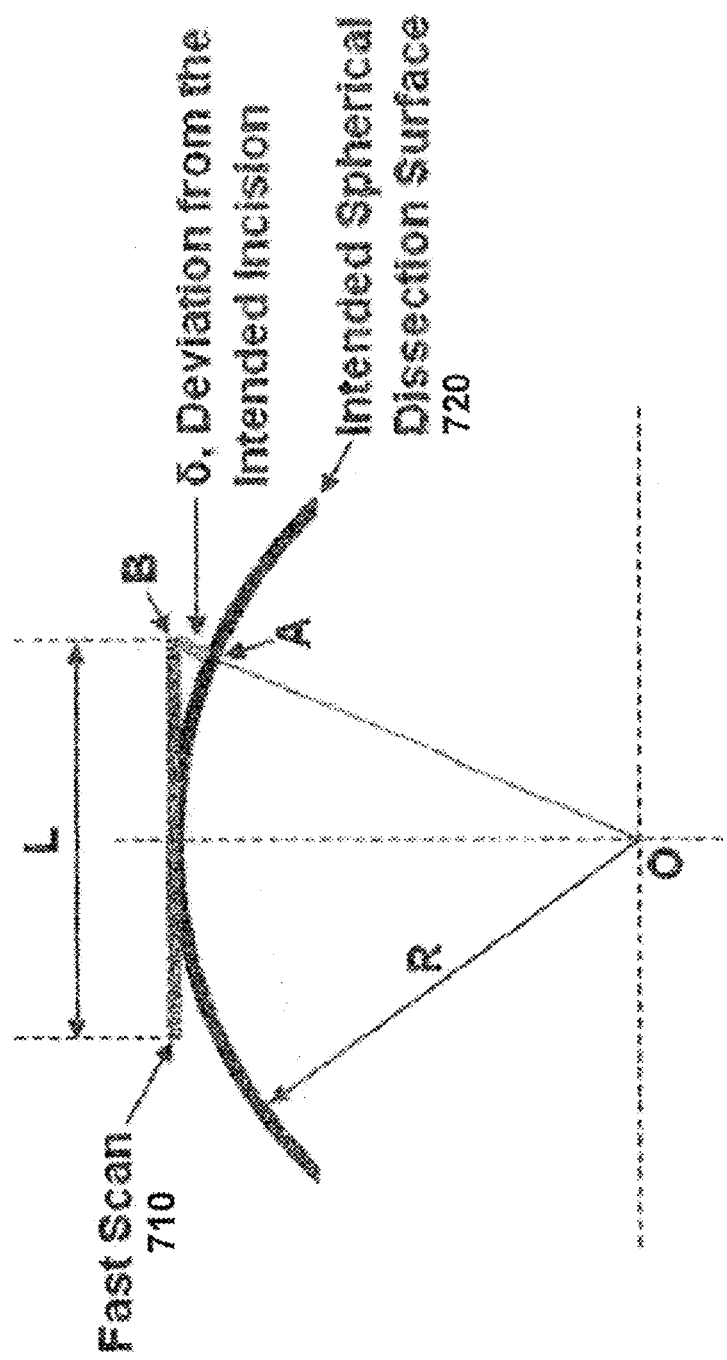
FIG. 7 illustrates a geometric relation between a fast scan line and an intended spherical dissection surface of a surgical ophthalmic laser system according to an embodiment of the present invention.

FIG. 7 shows the geometric relation between the fast scan line 710 and the intended spherical dissection surface 720, e.g., of a lens, especially the distance deviation (δ) between the end point B of the scan line 720 and point A on the intended dissection surface 720. The maximum deviation .delta. is the distance between point A and point B, and is given by $$\delta = \sqrt{R^2 + \frac{L^2}{4}} - R \approx \frac{L^2}{8R},, \qquad \text{equation (1)}$$

where R is greater than L. R is the radius of curvature of the surface dissection 720, and L is the length of the fast scan.

In an exemplary case of myopic correction, the radius of curvature of the surface dissection may be determined by the amount of correction, ΔD, using the following equation $$\Delta D = \frac{(n-1)}{R_1} + \frac{(n-1)}{R_2},, \qquad \text{equation (2)}$$

where n=1.376, which is the refractive index of cornea, and $R_1$ and $R_2$ (may also be referred herein as Rt and Rb) are the radii of curvature for the top surface and bottom surface of a lenticular incision, respectively. For a lenticular incision with $R_1=R_2=R$ (the two dissection surface are equal for them to physically match and be in contact), we have $$R = \frac{2(n-1)}{\Delta D},, \qquad \text{equation (3)}$$

Figure 8:
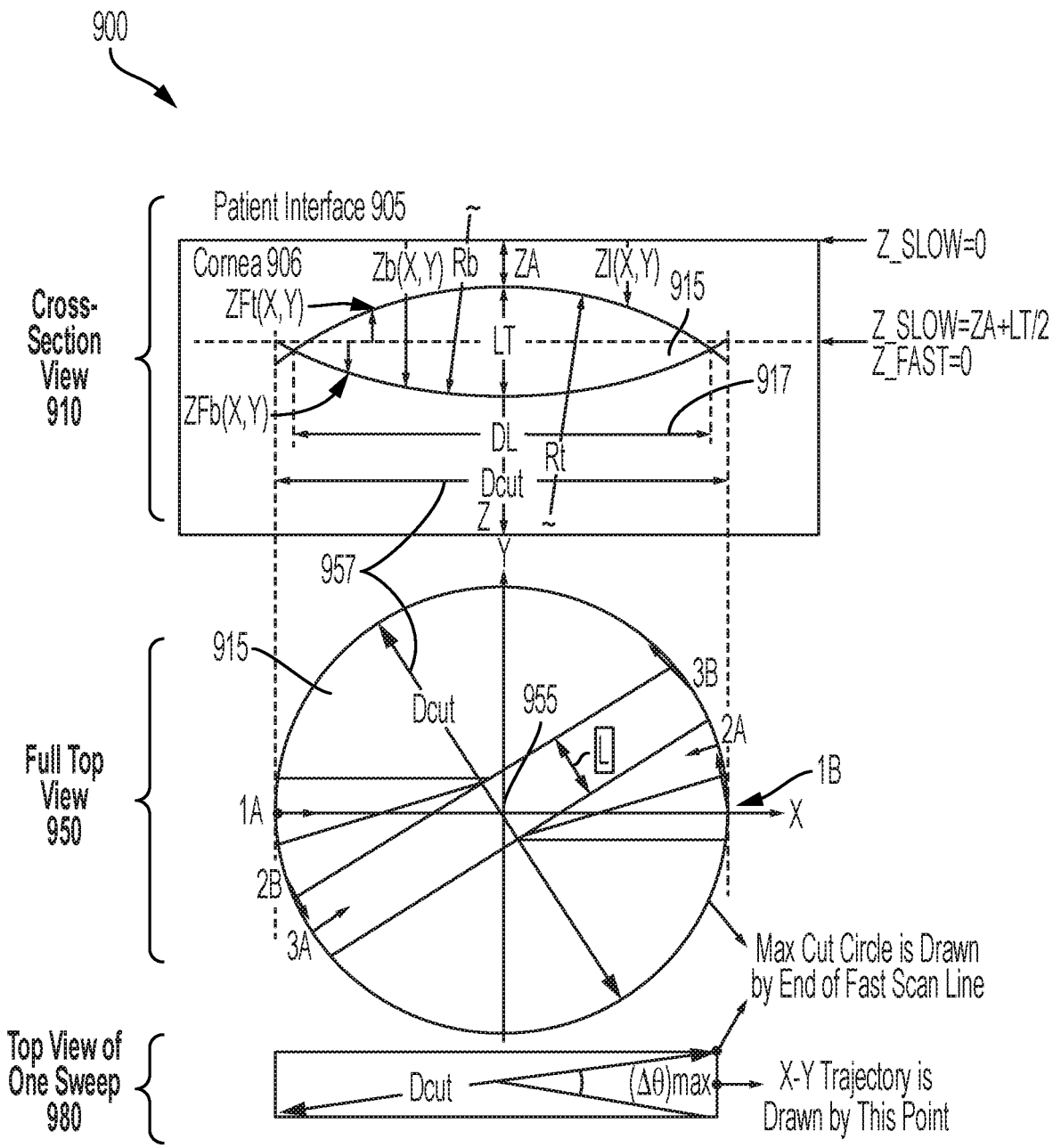
FIG. 8 illustrates an exemplary lenticular incision using a surgical ophthalmic laser system according to an embodiment of the present invention.

In an embodiment, FIG. 8 shows an exemplary lenticular incision 900 for extraction using the laser system 10. FIG. 8 shows an exemplary cross-sectional view 910 illustrating a patient interface 905 (or patient interface 31 as shown in FIG. 3), cornea 906, and lenticular incision volume 915, which will be referred herein as lens to be extracted. Rt and Rb are the radii of curvature for the top surface and bottom surface of a lenticular incision, respectively. ZFt (Zt) is the depth of the top surface of the lenticular incision. ZFb (Zb) is the depth of the bottom surface of the lenticular incision. The Z depths may be calculated based on the respective radii. LT is the lens thickness at the lens apex, or center thickness of the lens. ZA is depth of the lens apex. DL is the diameter of the lenticular incision, or the lens. {Z_SLOW=0} is the Z reference position before the laser system 10 calculates and sets Z_SLOW, e.g., {Z_SLOW=ZA+LT/2} the center depth of the lens, which remains fixed for the duration of the incision procedure. Z_SLOW may then be the reference position for the Z-scanner for top and bottom incision surfaces. In an embodiment, the diameter of the lens may be received from an operator of the laser system 10, or may be calculated by the laser system 10. The thickness of the lens may be determined, for example, by the total amount of correction (e.g., diopter) and the diameter of the lens.

A top view 950 of the lenticular incision 900 illustrates three exemplary sweeps (1A to 1B), (2A to 2B) and (3A to 3B), with each sweep going through (i.e., going over) the lenticular incision apex 955. The incision, or cut, diameter 957 ($D_{CUT}$) should be equal to or greater than the to-be-extracted lenticular incision diameter 917 (DL). A top view 980 shows the top view of one exemplary sweep. In an embodiment, the lenticular incision is performed in the following steps:

1. Calculate the radius of curvature based on the amount of correction, e.g., a myopic correction.
2. Select the diameter for the lenticular incision to be extracted.
3. Perform the side incision first (not shown) to provide a vent for gas that can be produced in the lenticular surface dissections. This is also the incision for the entry of forceps and for lens extraction.
4. Perform bottom surface dissection (the lower dissection as shown in cross-sectional view 910). In doing so, the fast scan line is preferably kept tangential to the parallels of latitude, and the trajectory of the slow sweep drawn by X, Y, and Z scanning devices moves along the meridians of longitude (near south pole in a sequence of 1A→1B (first sweep of lenticular cut), 2A→2B (second sweep of lenticular cut), 3A→3B (third sweep of lenticular cut), and so on, until the full bottom dissection surface is generated.

5. Perform the top surface dissection (the upper dissection as shown in the cross-sectional view 910) in a similar manner as the bottom dissection is done. It is noted that the bottom dissection is done first. Otherwise, the bubble generated during the top dissection will block the laser beam in making the bottom dissection.

For illustrative purposes, in a myopic correction of ΔD=10 diopter (i.e., 1/m), using equation (3), R=75.2 mm, which is indeed much greater than the length L of the fast scan. Assuming a reasonable scan line length of L=1 mm, using equation (1), the deviation δ=1.7 µm. This deviation is thus very small. For comparison purpose, the depth of focus of a one micron (FWHM) spot size at 1 µm wavelength is about ±3 µm, meaning the length of focus is greater than the deviation δ.

Figure 9:
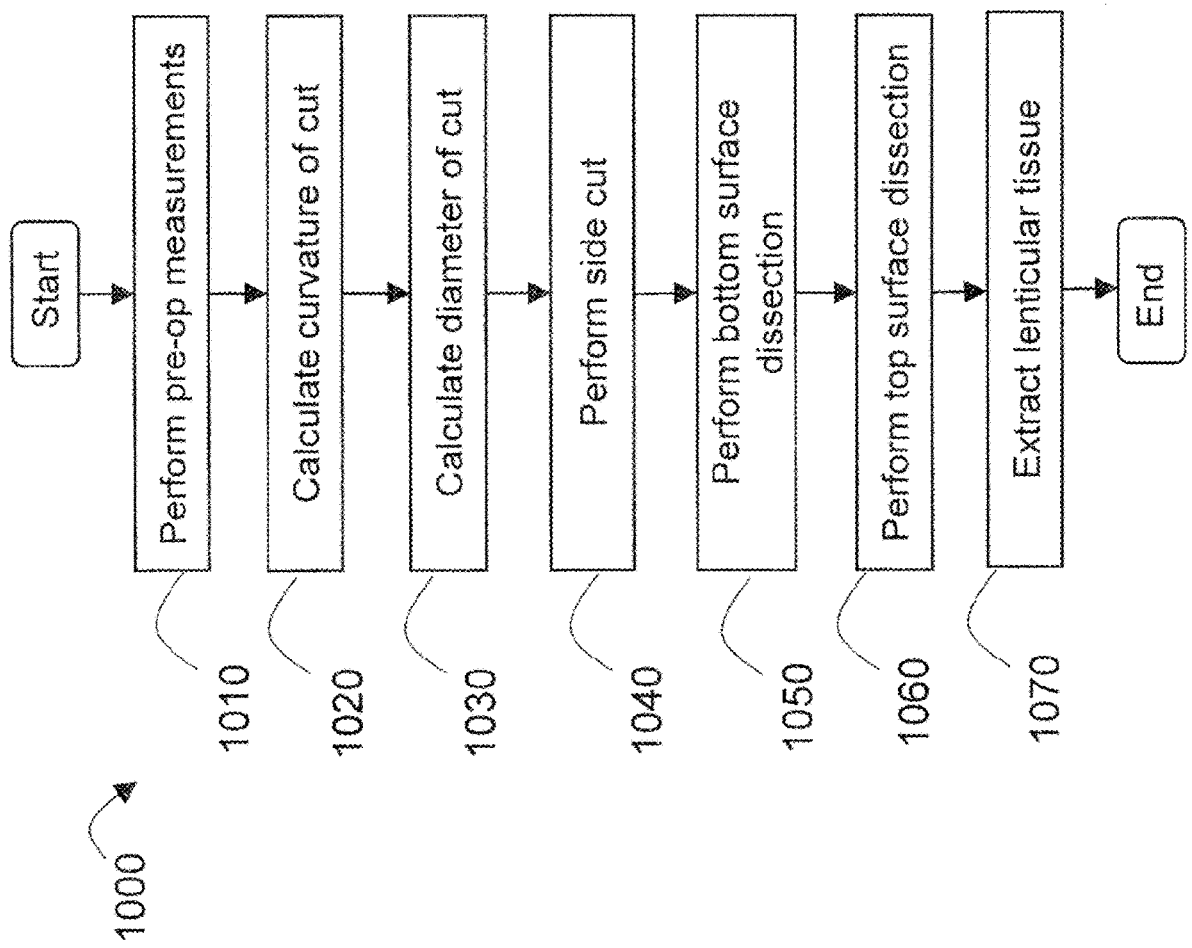
FIG. 9 is a flowchart illustrating a process according to an embodiment of the present invention.
Figure 10:
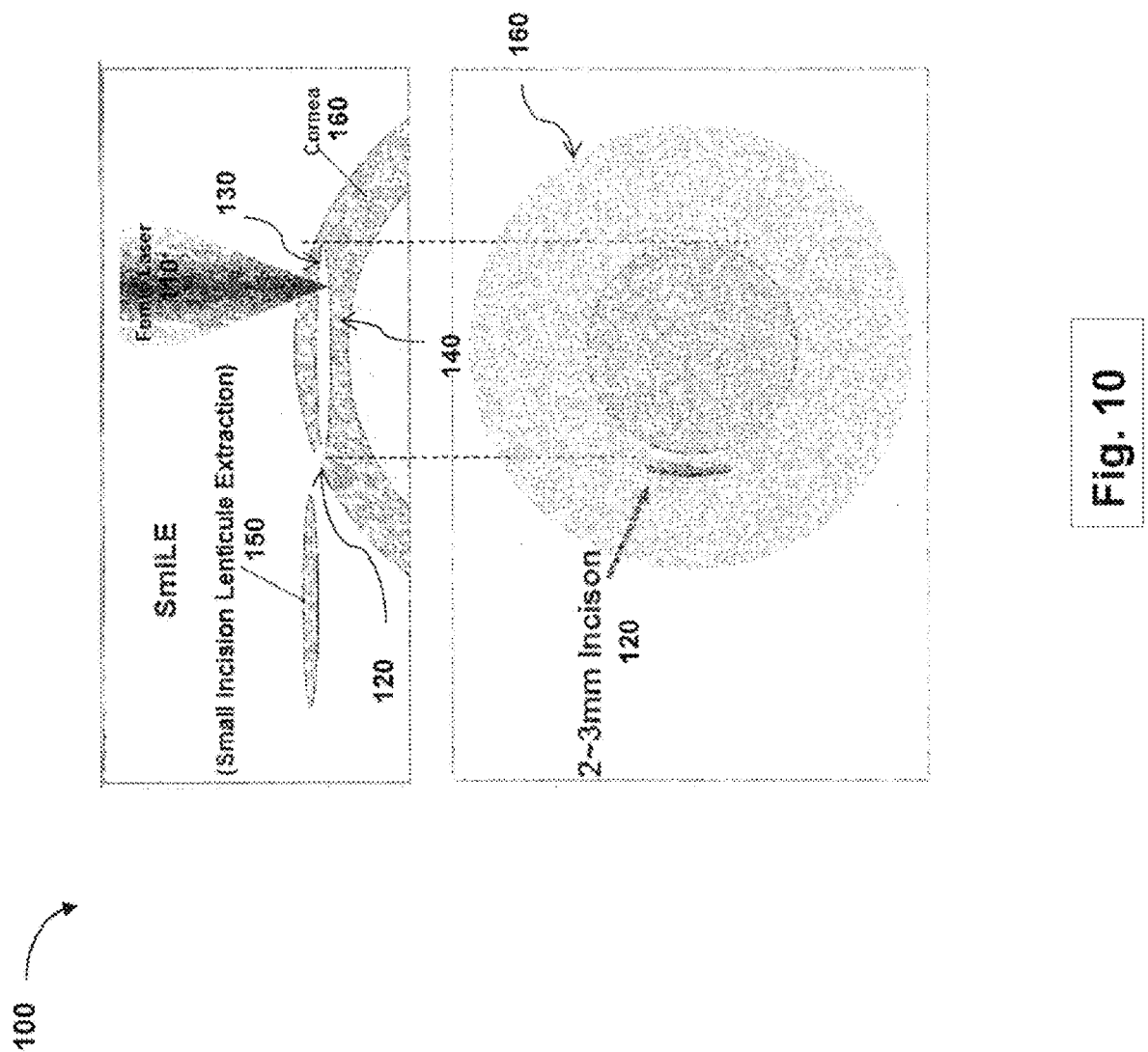
FIG. 10 illustrates a conventional Small Incision Lenticule Extraction procedure.

FIG. 9 illustrates a process 1000 of the laser system 10 according to an embodiment. The laser system 10 may start a surgical procedure performing pre-operation measurements (Action Block 1010). For example, in an ophthalmologic surgery for myopic correction, the myopic diopter is determined, the SLOW_Z position is determined, and so on. The laser system 10 calculates the radius of curvature based on the amount of correction, e.g., the myopic correction determined in pre-operation measurements (Action Block 1020), as shown, for example, in equations (2) and (3) above. The laser system 10 calculates the diameter of the incision (Action Block 1030), as shown by $D_{CUT}$ in FIG. 8. $D_{CUT}$ is equal to or greater than the diameter of the to-be-extracted lenticule (DL in FIG. 8). The laser system 10 first performs side incision to provide a vent for gas that can be produced in the lenticular surface dissections, and for tissue extraction later on (Action Block 1040). The laser system 10 then performs the bottom lenticular surface dissection (Action Block 1050) before performing the top lenticular surface dissection (Action Block 1060). The lenticular tissue is then extracted (Action Block 1070).

In other embodiments, the laser system 10 may also be used to produce other three-dimensional surface shapes, including toric surfaces for correcting hyperopia and astigmatism. The laser system 10 may also be used for laser material processing and micromachining for other transparent materials. Correction of hyperopia by the laser system 10 is discussed in detail below.

Figure 11:
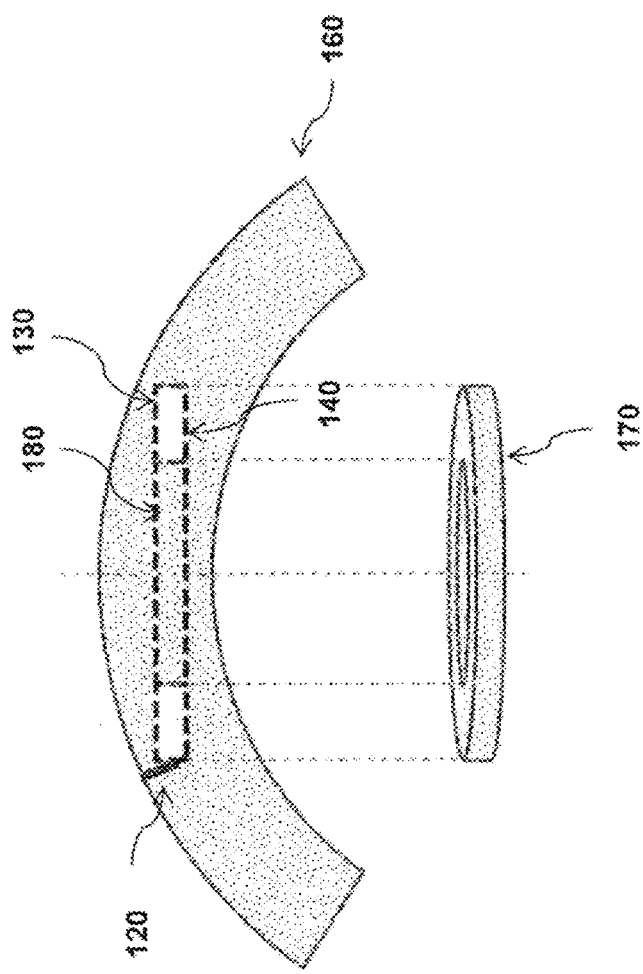
FIG. 11 illustrates a hypothetical Small Incision Lenticule Extraction procedure.

Conventional laser surgery methods to correct hyperopia utilize cut patterns including ring-shaped incision patterns that steepen the curvature of a cornea. However, FIG. 11 illustrates why utilizing these patterns using SmILE is impractical and unfeasible. The cross-sectional view of the cornea 160 in FIG. 11 includes a sidecut 120, an upper surface cut 130, lower surface cut 140 and a ring-shaped cut 170 generated by a SmILE procedure. However, the cornea 160 maintains an uncut annular center portion 180 that remains attached to an anterior portion and posterior portion of the cornea 160.

This cut pattern is geometrically problematic as the clean removal of the ring cut 170 through the side cut 120 as a single ring is impeded by the center portion 180. Whereas a flap provided in a LASIK procedure allows a ring shape to be easily extracted, the use of a sidecut without a flap prevents the ring-shaped stroma material from being extracted from the tunnel like incision without breaking apart. Thus, a ring-shaped lenticule is not suitable for correcting hyperopia using the SmILE procedure since the ring cut 170 will break up unpredictably during removal through the side cut 120.

Some LASIK procedures correct hyperopia by removing cornea stroma material to increase the steepness of the cornea. For example, outward portions of the cornea are cut and removed while a center portion remains untouched except for the flap. Once the flap is folded back over, the flap fills the void vacated by the removed cornea stroma material and merges with the cornea. The cornea thus becomes steeper and a desired vision correction is achieved. However, the curve of the flap does not match the curve of the cornea such that the merger of the flap and cornea creates folds in the stroma that increase light scattering and create undesirable aberrations.

Figure 12:
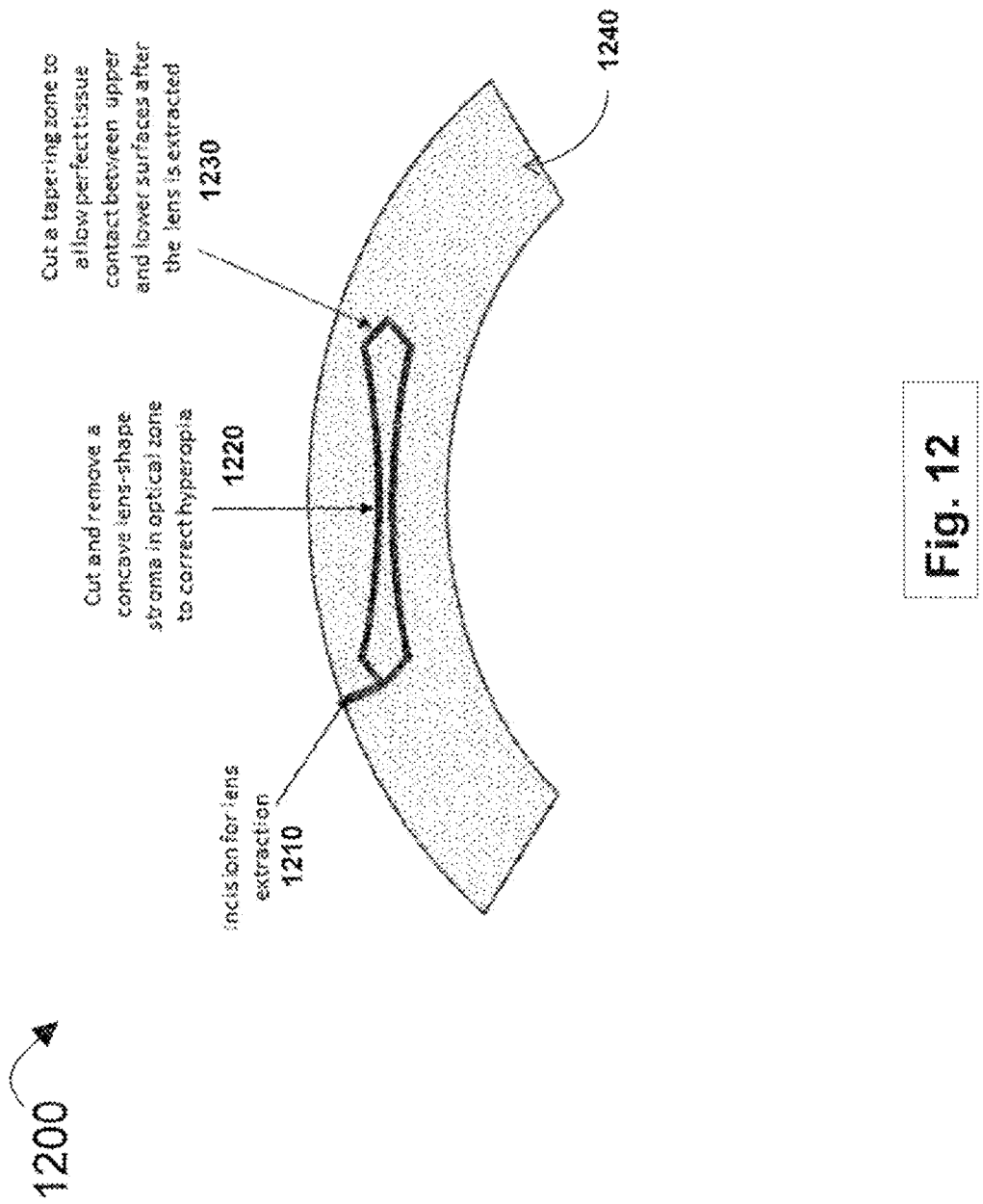
FIG. 12 illustrates an exemplary lenticular incision process according to an embodiment of the present invention.

The inventions described herein overcome these limitations. FIG. 12 illustrates an exemplary lenticular incision 1200 that steepens the cornea by cutting and removing a symmetric concave lens-shaped stroma material from a cornea 1240. From an optical focus power perspective, the concave shape of the lenticule 1220 is equivalent to steepening the cornea or adding a convex lens in front of the eye.

Figure 13:
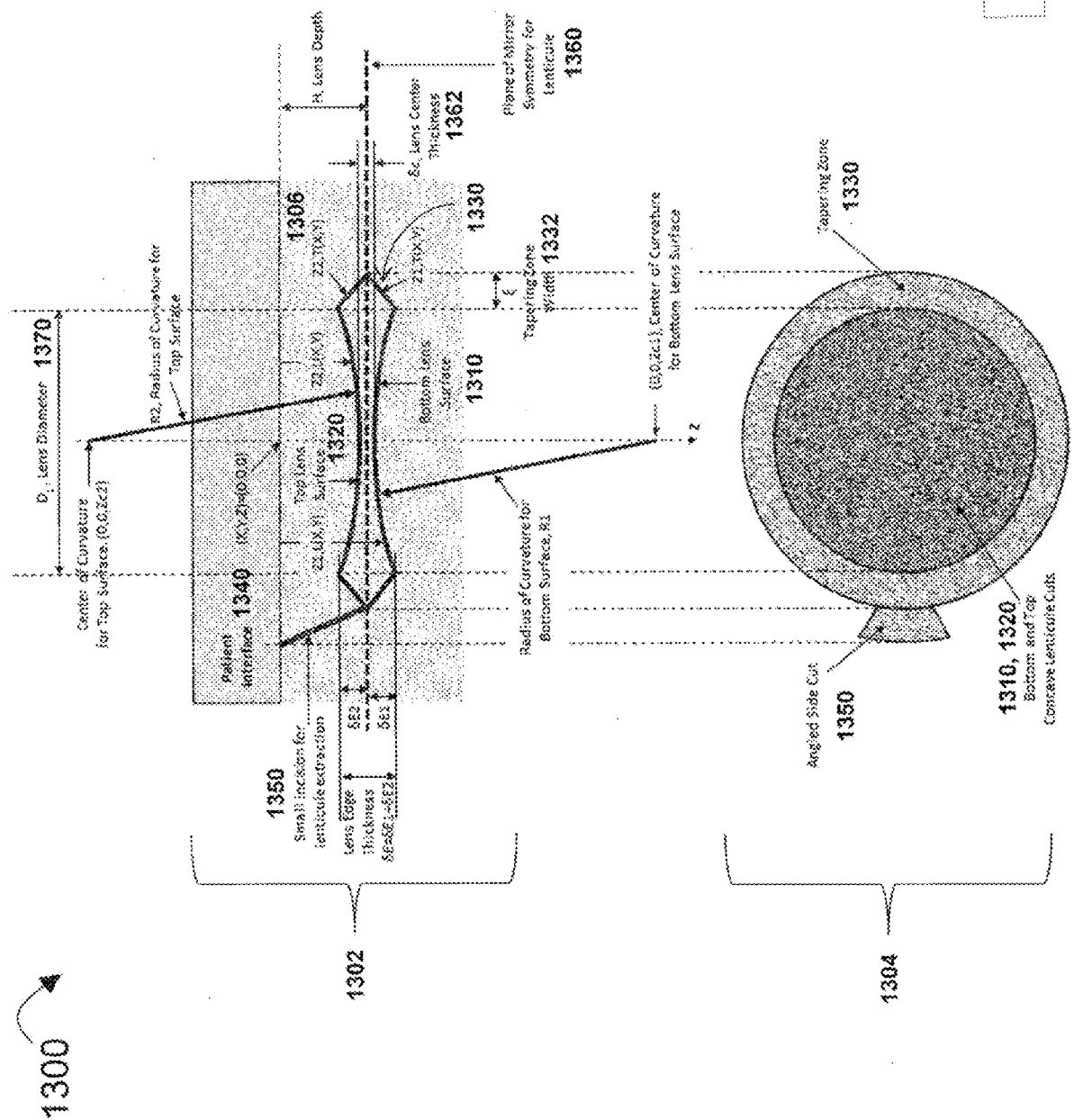
FIG. 13 illustrates an exemplary lenticular incision using a surgical ophthalmic laser system according to an embodiment of the present invention.

Furthermore, extraction of the lenticule 1220 as a whole piece through a sidecut incision 1210 is assured and improved over a ring-shape cut, or a tunnel-like cut, or a toric cut. The incision includes a peripheral portion 1230 or tapering portion providing ideal merging of the cornea after the lenticule 1220 is extracted without folding in a top surface or bottom surface. FIG. 13 illustrates an exemplary lenticular incision 1300 using a surgical ophthalmic laser system according to an embodiment of the present invention. For example, SmILE techniques may be applied in conjunction with FIG. 13 to treat hyperopia using a sub-nanosecond laser. A cross-sectional view 1302 and top view 1304 are provided of the lenticule cuts 1310, 1320 and side cut 1350. In FIG. 13, a patient interface 1340 is pressed against a cornea 1306. The lenticular incision includes a bottom lens surface 1310 and a top lens surface 1320. The bottom surface 1310 includes a radius of curvature $R_1$ and the top surface 1320 includes a radius of curvature $R_2$.

A side cut 1350 is performed first to provide a path for gas to vent to prevent the formation of bubbles. A bottom surface cut 1310 is then performed prior to performing a top surface cut 1320 to prevent the cutting beam from being blocked by bubbles generated by previous cornea dissection. The top and bottom surface cuts each include a central portion and a peripheral portion. The central portions are concave while the peripheral portions of the top and bottom cuts tapers (diminishes) towards each other to meet. The tapering peripheral portions minimize light scattering at the edges and further optimizes the matching of the cut surfaces and prevent folding after the lenticule has been removed.

As shown in FIG. 13, the thickest portion of the cut is provided at the boundary of the taper portion and the concave portion. For the top and bottom surfaces to match after lens extraction, the bottom and top surfaces are preferably mirror symmetric about a plane 1360.

These exemplary lenticular incisions allow lenticular tissue to be extracted in a single unbroken piece through the sidecut. The taper of the peripheral portions allows smooth extraction through the sidecut as a gradual slope is provided. The peripheral portions also support the merging of the top and bottom portions of the cornea as a top surface and bottom surface compress back together to form a smooth merge. Without a taper to the peripheral portions, the apex of the central portions would never merge and would form a permanent gap.

A concave lens cut includes a top concave lenticular incision and a bottom concave lenticular incision of a lens in the subject's eye. The concave lens cut may include at least one of a spherical surface, a cylindrical component, and any high order component. The top concave lenticular incision and the bottom concave lenticular incision may be mirror symmetric or nearly mirror symmetric to each other so long as the merging of the top surface and bottom surface does not create folding.

The system may operate with a laser having a wavelength in a range between 350 nanometer and 1100 nanometer and a pulse width in a range between 10 femtosecond and 1 nanosecond.

In prior art solutions, a top layer cut is longer than a bottom layer cut. Under this configuration, the top and bottom cornea portions do not ideally merge as the top surface must fold in and compress in order to merge with shorter layer cut. With this fold created by the dissection, light scattering is increased. In contrast, a mirror symmetric cut along a center line allows ideal merge with no folding between a top layer and bottom layer. Consequently, there is less light scattering.

A lens edge thickness is given by $\delta_E$, $\delta_{E1}$, $\delta_{E2}$. A lens depth H is given as a distance between an anterior of the cornea 1306 and the plane 1360. The bottom surface 1310 and top surface 1320 have a lens diameter DL, a lens center thickness .delta.c and a shape defined by respective curves $Z_{1,L(x,y)}$ and $Z_{2,L(x,y)}$. In order to minimize the amount of dissected cornea stroma material removed, the central thickness .delta.c should be minimized. For example, the central thickness may be a few μm, which can be achieved by using a laser beam with a high numerical aperture (such as NA=0.6).

Each of the bottom lens surface cut 1310 and the top lens surface cut 1320 includes a tapering zone 1330 along a periphery of the cuts. The tapering zone 1330 is defined by a tapering zone width $\xi$ and the curves $Z_{1,T(x,y)}$ and $Z_{2,T(x,y)}$.

A sidecut 1350 is provided from a surface of the cornea to the tapering zone 1330 for removal of the lenticule. The sidecut may meet the tapering zone 1330 on the mirror plane 1360 or other suitable extraction point.

With these parameters as described and illustrated, a set of equations are provided below that determine the three-dimensional shape of the lenticular cuts, assuming that the desired correction is purely defocus:

$$Z_{1,L}(x, y) = H + \frac{\delta_C}{2} + R_1 - \sqrt{R_1^2 - x^2 - y^2} \text{ for}$$
$$\sqrt{x^2 + y^2} \leq \frac{D_L}{2}$$
Eq. (4)

$$Z_{2,L}(x, y) = H - \frac{\delta_C}{2} - R_2 + \sqrt{R_2^2 - x^2 - y^2} \text{ for}$$
$$\sqrt{x^2 + y^2} \leq \frac{D_L}{2}$$
Eq. (5)

$$Z_{1,T}(x, y) = H + \delta_{E1} - \left(\sqrt{x^2 + y^2} - \frac{D_L}{2}\right) \cdot \frac{\delta_{E1}}{\xi} \text{ for}$$
$$\frac{D_L}{2} \leq \sqrt{x^2 + y^2} \leq \frac{D_L}{2} + \xi$$
Eq. (6)

$$Z_{2,T}(x, y) = H - \delta_{E2} + \left(\sqrt{x^2 + y^2} - \frac{D_L}{2}\right) \cdot \frac{\delta_{E2}}{\xi} \text{ for}$$
$$\frac{D_L}{2} \leq \sqrt{x^2 + y^2} \leq \frac{D_L}{2} + \xi$$
Eq. (7)

$$\delta_{E1} = \frac{\delta_C}{2} + R_1 - \sqrt{R_1^2 - \left(\frac{D_L}{2}\right)^2}$$
Eq. (8)

$$\delta_{E2} = \frac{\delta_C}{2} + R_2 - \sqrt{R_2^2 - \left(\frac{D_L}{2}\right)^2}$$
Eq. (9)

The shape and dimensions of the cuts may include additional correction for higher order aberrations and may be computed from measured vision errors. In some embodiments, approximately 50% of the total hyperopic correction is applied to each of the two mutually mirror-imaged cut surfaces.

It is noted that the thickest portion of the concave lens cut is provided at the intersection of the tapering zone and the concave lens cuts which correspond to a portion of the cornea that is thicker than a center portion of the cornea. Consequently, from the standpoint of cornea thickness, correcting hyperopia is more tolerable than correcting myopia, where the thicker portion of the lens to be removed is at the center of the cornea, corresponding to a thinner portion of the cornea.

The shape of the tapering zone 1330 need not be linear in shape. The tapering zone may be curved or any shape that minimizes light scattering at the cutting junctions and optimizes the matching of the two cut surfaces after lens extraction. The peripheral zone may be linear or a higher order polynomial.

Some embodiments of the invention apply to single-spot scanning methods applied in femtosecond laser systems. The invention also applies to cornea incisions using UV 355 nm sub-nanosecond lasers.

For illustrative purposes, Equations (2), (8) and (9) are used to estimate the thickness of the concave lens. In a hyperopic correction of $\Delta D=5$ diopter (which is high end values for LASIK hyperopia procedures) and assuming that a symmetric shape of the lenticule is selected, $R_1=R_2=150.4$ mm. Assuming $D_L=7.0$ mm and $\delta_C=10$ μm, then $\delta_E=\delta_{E1}+\delta_{E2}\approx\delta_C+D_L^2*\Delta D/[8(n-1)]\approx 92$ μm.

Figure 14:
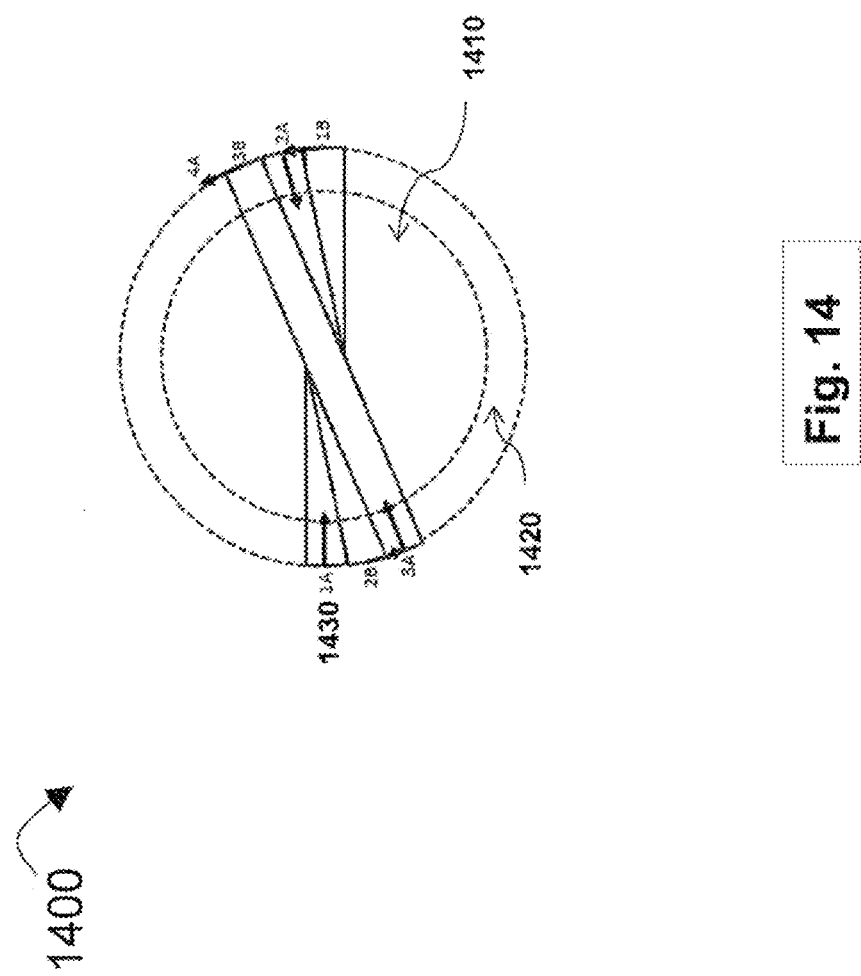
FIG. 14 illustrates an exemplary scanning process using a surgical ophthalmic laser system according to an embodiment of the present invention.

FIG. 14 illustrates an exemplary scanning process 1400 using a surgical ophthalmic laser system according to an embodiment of the present invention. FIG. 14 illustrates another embodiment of the "Fast-Scan-Slow-Sweep" scanning described previously. While performing an XY scan, Z values can be calculated from Eqs. (1)-(9), and the desired three-dimensional concave lens-shape cutting surfaces may be generated.

A top view of the lenticular incision illustrates three exemplary sweeps 1430 (1A to 1B), (2A to 2B) and (3A to 3B), with each sweep going through (i.e., going over) the concave lenticular incision 1410 and tapering zone 1420. In an embodiment, the lenticular incision is performed in the following steps:

1. Calculate the radius of curvature based on the amount of correction, e.g., a hyperopic correction.

2. Select the diameter for the lenticular incision to be extracted.

3. Calculate the shape of the lenticular incisions (concave surface and taper).

4. Perform the side incision first (not shown) to provide a vent for gas that can be produced in the lenticular surface dissections. This is also the incision for the entry of forceps and for lens extraction.

5. Perform bottom surface dissection (the bottom dissection 1310 as shown in cross-sectional view). In doing so, the fast scan line is preferably kept tangential to the parallels of latitude, and the trajectory of the slow sweep drawn by X, Y, and Z scanning devices moves along the meridians of longitude (near south pole in a sequence of 1A→1B (first sweep of lenticular cut), 2A→2B (second sweep of lenticular cut), 3A→3B (third sweep of lenticular cut), and so on (4A), until the full bottom dissection surface is generated.

6. Perform the top surface dissection 1320 in a similar manner as the bottom dissection is done. It is noted that the bottom dissection is done first. Otherwise, the bubble generated during the top dissection will block the laser beam in making the bottom dissection.

Figure 15:
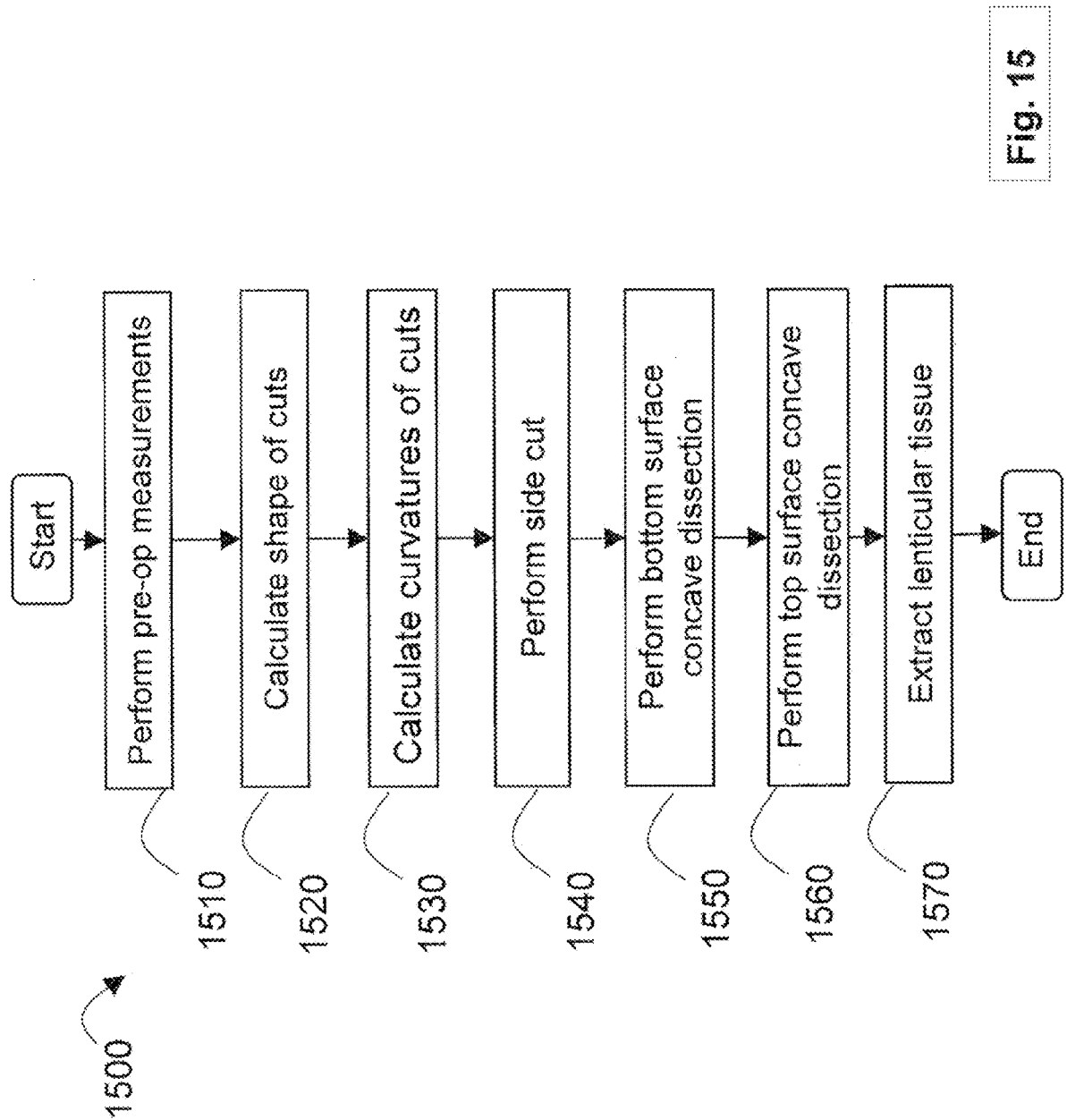
FIG. 15 is a flowchart illustrating an exemplary surgery process according to an embodiment of the present invention.

FIG. 15 is a flowchart illustrating an exemplary surgery process 1500 according to an embodiment of the present invention. The laser system 10 may start a surgical procedure performing pre-operation measurements (Action Block 1510). For example, in an ophthalmologic surgery for hyperopic correction, the hyperopic diopter is determined, the SLOW_Z position is determined, and so on. The laser system 10 calculates the shape of the incisions (Action Block 1520). The laser system 10 calculates the radius of curvatures based on the amount of correction, e.g., the hyperopic correction determined in pre-operation measurements (Action Block 1530), as determined by Equations (4)-(8), for example. The laser system 10 first performs a side incision to provide a vent for gas that can be produced in the lenticular surface dissections, and for tissue extraction later on (Action Block 1540). The laser system 10 then performs the bottom lenticular surface dissection (Action Block 1550) before performing the top lenticular surface dissection (Action Block 1560). Performing the dissections in this order allows gas to vent out of the cornea instead of becoming trapped in gas bubbles within the cornea. The lenticular tissue is then extracted (Action Block 1570).

Figure 16:
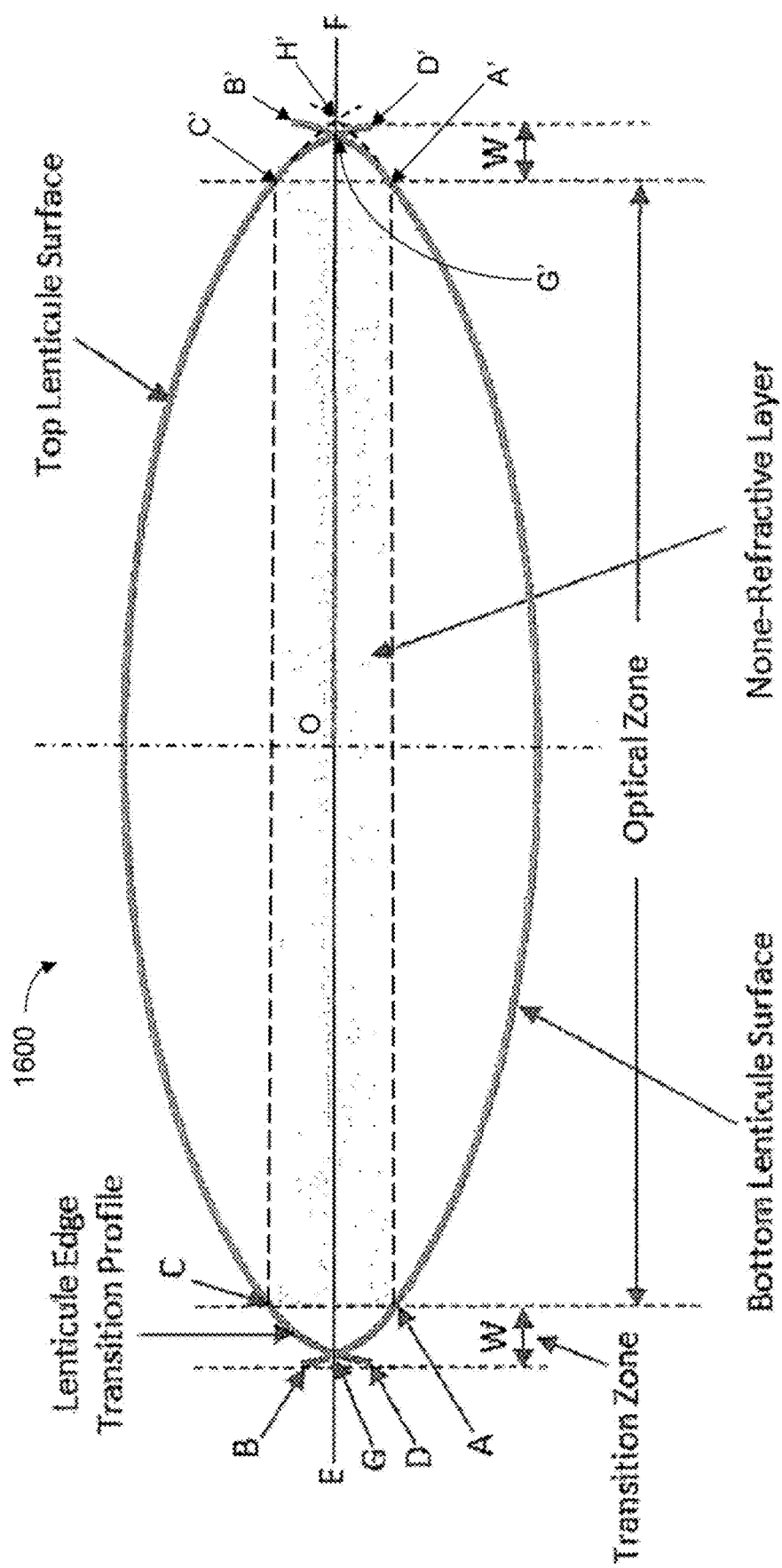
FIG. 16 illustrates an exemplary lenticular incision using a surgical ophthalmic laser system according to another embodiment of the present invention.

Another embodiment for creating a lenticular incision for treating myopia, by cutting and extracting a convex lens-shaped stroma material from a corneal, is described with reference to FIG. 16. FIG. 16 is a side cross-sectional view of the lenticular incision 1600 cut through the optical axis, where the vertical direction is the depth direction, parallel to the optical axis of the eye, and the horizontal direction is referred to as the transverse direction. The lenticular incision 1600 preferably has a circular shape in the front view of the eye. In some embodiments, the lenticular incision 1600 is rotationally symmetrical with respect to the optical axis of the eye. The cornea from which the lenticule is incised and extracted is not shown. This procedure is intended to be performed using a patient interface (not shown) that does not employ a contact lens to press against the patient's cornea. Such a patient interface may employ, for example, a liquid that fills the space between the patient's cornea and a lens of the patient interface. Thus, the cornea is in its natural shape during the creation of the lenticular incision.

The lenticular incision 1600 in this embodiment is similar to the lenticular incision 900 in the embodiment of FIG. 8, with the following differences. The lenticular incision 900 in FIG. 8 is formed by a top lenticular surface and a bottom lenticular surface which are both convex spherical surfaces (i.e. each is a part of a sphere). In the lenticular incision 1600 of FIG. 16, each of the top and bottom lenticular surfaces has a convex spherical portion CC' or AA' at the center, and a peripheral portion CD or AB, referred to as the edge transition portion. In the top view, the spherical portion preferably has a circular shape and the edge transition portion has a ring shape that surrounds the spherical portion; the top and bottom spherical portions overlap each other in the top view and the top and bottom edge transition portions overlap each other. While each of the top and bottom spherical portions is a part of a sphere, the respective edge transition portion is not located on the same sphere of the spherical portion but rather, has a steeper shape in the side cross-sectional view than the sphere. In other words, each edge transition portion is located within the volume defined by the sphere of the corresponding spherical portion. Thus, the distance from the optical axis O of the lenticule to the intersection point G, where the top edge transition portion CD and the bottom edge transition portion AB intersect each other, is smaller than the distance from the optical axis O to the imaginary intersection point H', where the two spheres that define the spherical portions CC' and AA' intersect each other. Note that, in FIG. 16, the two intersection points are illustrated on the right-hand side edge of the lenticule 1600 and labeled G' and H', respectively, where OG'<OH'.

The central portion of the lenticule 1600 insider the peripheries of the spherical portions CC' and AA' of the top and bottom lenticule surfaces constitutes the optical zone of the lenticule; the optical power of the optical zone is defined by the curvatures of the top and bottom spherical portions. Within the optical zone, a center layer, located between a transverse plane that pass through the circumference of the top spherical portions CC' and a transverse plane that pass through the circumference of the bottom spherical portions AA', which are indicated by the two horizontal dashed lines in FIG. 16, constitutes a non-refractive layer as it does not contribute to the optical power of the optical zone.

In some preferred embodiment, the distance (denoted $W_G$) from the boundary of the optical zone (in FIG. 16, the line parallel to the optical axis O and passing through the boundary C of the optical zone) to the intersection point G of the two edge transition portions is between 30% to 90% of the distance (denoted $W_H$) from the boundary of the optical zone to the imaginary intersection point H', i.e., $30\% < W_G/W_H < 80\%$. In some preferred embodiment, in the side cross-sectional view (e.g. FIG. 16), the edge transition portion CD is a part of an ellipse, with the major axis of the ellipse oriented parallel to the optical axis O and the minor axis perpendicular to the optical axis O. In such an example, the width of the edge transition portion (i.e. the distance $W_G$) can be adjusted by adjusting the minor axis of the ellipse.

The side cross-sectional profiles of the top and bottom edge transition portions CD and AB are smooth functions, i.e., their first order derivatives are continuous functions. Moreover, each of the top and bottom lenticular surface profiles is smooth at the point where the spherical portion CC'/AA' joins the edge transition portion CD/AB. In other words, the entire top lenticular surface is a smooth surface and the entire bottom lenticular surface is a smooth surface. This reduces tissue step formation in the cornea after the lenticule is extracted.

The top and bottom edge transition portions CD and AB are mirror symmetrical with respect to the center plane EF, which is the transverse plane that passes through the intersection circle of the top and bottom edge transition portions CD and AB. Thus, the top and bottom incision surfaces have equal area, so that they will match each other without corneal striae after the lenticule is extracted. The top and bottom spherical portions CC' and AA' may be either mirror symmetrical or not mirror symmetrical with respect to the center plane EF.

The end points D and B of the top and bottom edge transition portions CD and AB extend beyond the intersection point G of the two edge transition portions. This helps to ensure that the lenticule is fully separated from the cornea, so that the extraction can be done free of tissue-bridges and minimal or no unwanted residual tissue pieces are left inside the cornea. In this regard, the lenticular incision 1600 is similar to the lenticular incision 900 of the embodiment of FIG. 8.

The lenticular incision 1600 of the embodiment of FIG. 16, with the edge transition portions in the periphery of the lenticule, has the following advantages over the lenticular incision 900 of the embodiment of FIG. 8. First, comparing a lenticule 900 and a lenticule 1600 having the same optical zone diameter (the optical zone of the lenticule 900 is the entire lenticule with incision diameter 917 (DL) as shown in FIG. 8), the shape of the lenticule 1600 effectively adds the non-refractive layer (a flat tissue disk of a certain thickness) to the lenticule. This can help ensure that the overall lenticule is sufficiently thick for it to be extracted as a whole piece. This is particularly important for low diopter correction (for example, less than 2 diopters), as the overall lenticule would otherwise be too thin. Second, the shape of the lenticule 1600 in the embodiment of FIG. 16 also increases the thickness of lenticule edge, due to the steeper profile in the edge transition regions CD and AB. This helps to ensures that the lenticule edge is sufficiently thick so it is much less likely to be torn during extraction. Torn edge would leave irregularly shaped residual tissue edge in the cornea.

A lenticule with an abrupt edge, such as that shown in FIG. 17A, can also solve the above two problems, by providing a lenticule edge with a non-zero thickness. Such a shape, however, has its own problems, one of which being that it leads to corneal striae after the lenticule is extracted and a remaining abrupt step is left in the cornea, as shown in FIG. 17B. Such unwanted abrupt change in the tissue can cause unwanted light scattering for the patient.

The lenticular incision 1600 of the embodiment of FIG. 16 solves the above two problems without creating a remaining abrupt step in the cornea after extraction.

To summarize, the lenticular incision 1600 of the embodiment of FIG. 16 has advantages over both the lenticular incision 900 of the embodiment of FIG. 8 and one with an abrupt edge as shown in FIG. 17A. The lenticular incision 1600 provides a continuous edge transition in the incision without abrupt steps; it allows for smooth intrastromal tissue matching in the vicinity of the lenticule edge after the lenticule is extracted, which minimizes corneal striae and light scattering that can be caused by abrupt tissue steps inside the cornea, and at the same time creates a lenticule of a sufficient thickness to ensure successful extraction.

The lenticular incision 1600 also has certain similarities with the hyperopia-correction lenticular incision 1200 and 1300 in the embodiment of FIGS. 12 and 13. Both the lenticular incision 1600 and the lenticular incision 1200/1300 has central portions of their top and bottom lenticular surfaces that are spherical, giving optical power to the lenticule, and peripheral portions that are not on the same spherical surface as the respective spherical portions, which serve as a transition region to avoid an abrupt edge and the problems associated with it.

Figure 19:
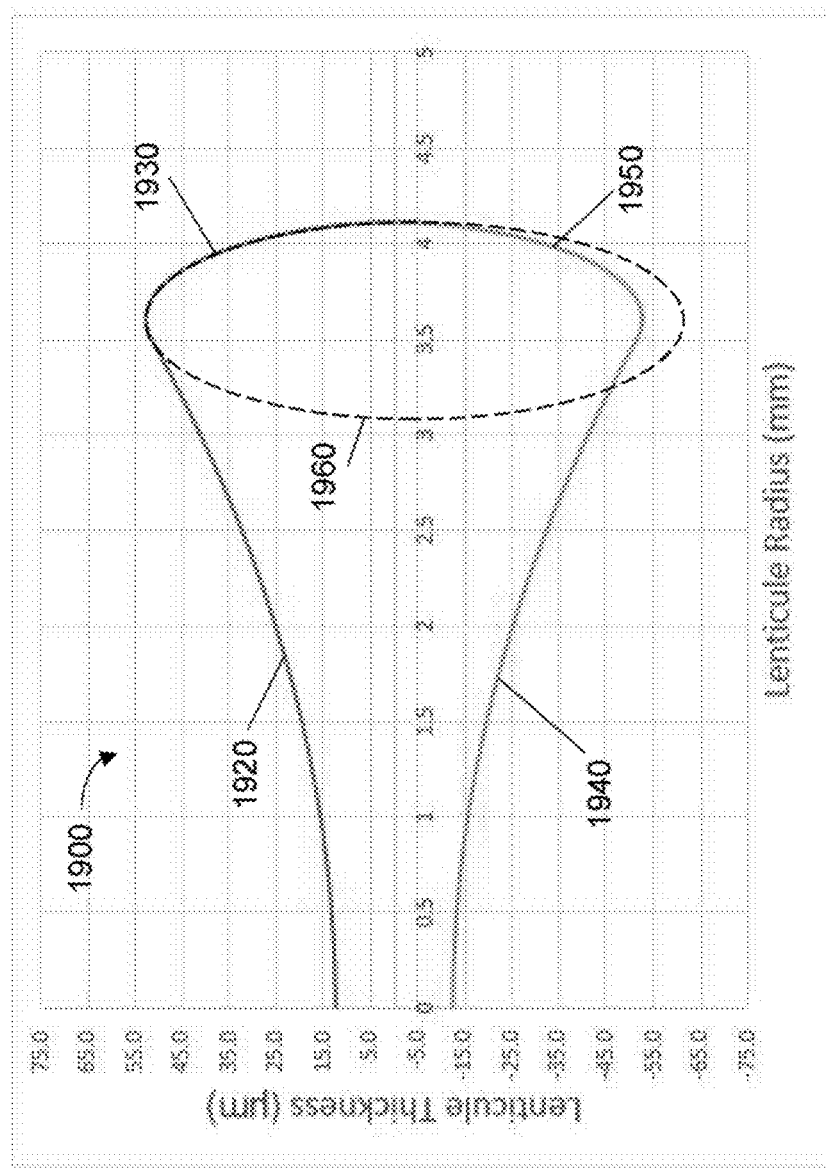
FIG. 19 illustrates a part of a lenticular incision according to another embodiment of the present invention.

FIG. 19 shows a variation of the lenticular incision 1200 or 1300 of FIGS. 12 and 13. The lenticular incision 1900 here (only half of it is shown in FIG. 19) is similar to the incisions 1200 and 1300 in that it has concave top and bottom surfaces 1920 and 1940, which are preferably spherical surfaces, and which define the optical power of the lenticule; but unlike in the incisions 1200 and 1300, the top and bottom edge transition portions 1930 and 1950 of the lenticular incision 1900 are smooth surfaces without sharp corners or edges. In one embodiment, in the side cross-sectional view (e.g. FIG. 19), the top edge transition portion 1930 is a part of an ellipse 1960, which is shown in dashed line in FIG. 19, with the major axis of the ellipse oriented parallel to the optical axis of the cornea and the minor axis perpendicular to the optical axis. The concave top surface joins the ellipse smoothly. Similarly, the bottom edge transition portion 1950 is also a part of another ellipse (not shown in FIG. 19). Preferably, the top and bottom edge transition portions 1930 and 1950 are mirror symmetrical to each other with respect to a transverse center plane perpendicular to the optical axis of the eye, and the top and bottom edge transition portions intersect each other at an intersection location and both extend beyond the intersection location.

The lenticular incisions 1600 and 1900 may be formed using a surgical ophthalmic laser system and the "Fast-Scan-Slow-Sweep" scanning method described previously. The scanning method is similar to that of the embodiments of FIG. 8 an FIGS. 13 and 14, except that in the side cross-sectional view the slow sweep follows the curve D-C-C'-D' for the top incision surface and the curve B-A-A'-B' for the bottom incision surface. In the top view, the sweeps are similar to those shown in FIG. 14, with exemplary sweeps 1A to 1B, 2A to 2B, and 3A to 3B, except that the central area 1410 would now indicate the spherical portion CC'/AA' (the optical zone), and the peripheral area 1420 would now indicate the edge transition portion CD/AB.

In an embodiment, the lenticular incision is performed in the following steps:

1. Calculate the radius of curvature of the spherical portions based on the amount of correction, e.g., a myopic correction.

2. Select parameters of the lenticular incision to be extracted, including the diameter of the optical zone and the thickness of the non-refractive layer.

3. Calculate the shape of the lenticular incisions (top and bottom spherical portions and top and bottom edge transition portions).

4. Perform the side incision first (not shown) to provide a vent for gas that can be produced in the lenticular surface dissections. This is also the incision for the entry of forceps and for lens extraction.

5. Perform bottom surface dissection. In doing so, the fast scan line is preferably kept tangential to the parallels of latitude (circles on the bottom lenticular surface that are perpendicular to and center at the optical axis), and the trajectory of the slow sweep drawn by X, Y, and Z scanning devices moves along the meridians of longitude (the curves formed by an intersection of the bottom lenticular surface with a side cut plane that passes through the optical axis) near south pole in a sequence of 1A to 1B (first sweep of lenticular cut), 2A to 2B (second sweep of lenticular cut), 3A to 3B (third sweep of lenticular cut), and so on (4A), until the full bottom dissection surface is generated.

6. Perform the top surface dissection in a similar manner as the bottom dissection is done. It is noted that the bottom dissection is done first. Otherwise, the bubble generated during the top dissection will block the laser beam in making the bottom dissection.

Figure 18:
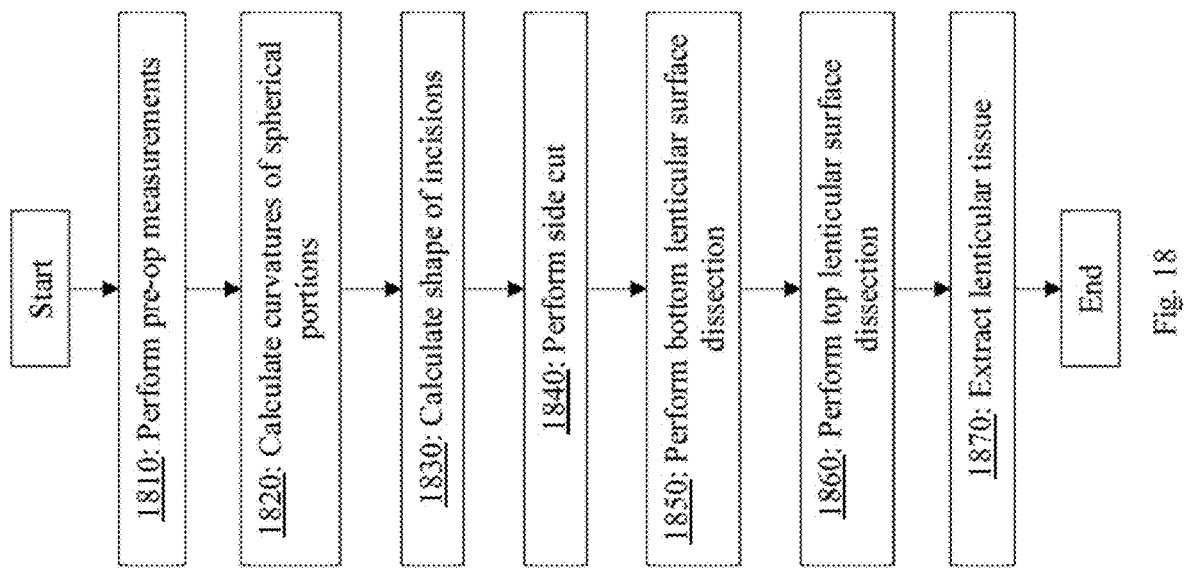
FIG. 18 is a flowchart illustrating an exemplary surgery process according to an embodiment of the present invention.

FIG. 18 is a flowchart illustrating an exemplary surgery process 1800 according to an embodiment of the present invention. The laser system 10 may start a surgical procedure performing pre-operation measurements (Action Block 1810). For example, in an ophthalmologic surgery for myopic correction, the myopic diopter is determined, the SLOW_Z position is determined, and so on. The laser system 10 calculates the radius of curvatures of the spherical portions based on the amount of correction, e.g., the myopic correction determined in pre-operation measurements (Action Block 1820). The laser system 10 calculates the shape of the incisions, including the edge transition portions according to the embodiment of FIG. 16 (Action Block 1830). The laser system 10 first performs a side incision to provide a vent for gas that can be produced in the lenticular surface dissections, and for tissue extraction later on (Action Block 1840). The laser system 10 then performs the bottom lenticular surface dissection (Action Block 1850) before performing the top lenticular surface dissection (Action Block 1860). Performing the dissections in this order allows gas to vent out of the cornea instead of becoming trapped in gas bubbles within the cornea. The lenticular tissue is then extracted (Action Block 1870).

In alternative embodiments, the optical zone of the lenticular incision 1600 may have non-spherical components, such as a cylindrical component or other higher order. In such a case, the central portion CC' and AA' are no longer spherical, but the edge transition portions CD and AB still have the characteristics that they are steeper than the extensions of the central portions would be.

As described earlier, the lenticular incision 1600 is intended to be performed using a patient interface that does not employ a contact lens to press against the patient's cornea, so that the cornea is in its natural shape during the creation of the lenticular incision. In an alternative embodiment, the lenticular incision may be performed while using a patient interface that presses against the cornea with a curved contact lens surface. In this case, the profiles of the top and bottom edge transition portions are substantially symmetrical about a center curved surface, rather than a transverse center plane. The shape of the center curved surface can be calculated from the shape of the contact lens surface, and is such that when the contact lens is removed from the patient's eye and the cornea returns to its natural shape, the center curved surface would become a transverse plane perpendicular to the optical axis.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. An ophthalmic surgical laser system comprising:
   a laser delivery system for delivering a pulsed laser beam to a target in a subject's eye;
   an XY-scan device to deflect the pulsed laser beam;
   a Z-scan device to modify a depth of a focus of the pulsed laser beam; and
   a controller configured to control the XY-scan device and the Z-scan device to form a top lenticular incision and a bottom lenticular incision of a lens in a cornea of the subject's eye, wherein the top lenticular incision has a top convex spherical portion at a center and a top edge transition portion that surrounds the top spherical portion, the top spherical portion being a part of a first sphere, the top edge transition portion being not a part of the first sphere and being located within a volume defined by the first sphere, the top lenticular incision being a smooth surface, wherein the bottom lenticular incision has a bottom convex spherical portion at a center and a bottom edge transition portion that surrounds the bottom spherical portion, the bottom spherical portion being a part of a second sphere, the bottom edge transition portion being not a part of the second sphere and being located within a volume defined by the second sphere, the bottom lenticular incision being a smooth surface, wherein the top and bottom edge transition portions are mirror symmetrical to each other with respect to a transverse center plane perpendicular to an optical axis of the eye, and wherein the top and bottom edge transition portions intersect each other at an intersection location and both extend beyond the intersection location such that the overall lenticule is sufficiently thick to be extracted as a whole piece and the lenticule edge is sufficiently thick to reduce the likelihood of it being torn during extraction.

2. The ophthalmic surgical laser system of claim 1, wherein in a side cross-sectional view, the top edge transition portion is a part of an ellipse, and the bottom edge transition portion is a part of another ellipse.

3. The ophthalmic surgical laser system of claim 1, further comprising a resonant scanner.

4. The ophthalmic surgical laser system of claim 1, wherein the XY-scan device deflects the pulsed laser beam to form a scan line.

5. The ophthalmic surgical laser system of claim 4, wherein the scan line is tangential to the parallels of latitude of the lens, the parallels of latitude being circles on the top or bottom lenticular surface that are perpendicular to and center at the optical axis.

6. The ophthalmic surgical laser system of claim 5, wherein the scan line is moved along the meridians of longitude of the lens, the meridians of longitude being curves formed by an intersection of the top or bottom lenticular surface with side cut planes that pass through the optical axis.

7. The ophthalmic surgical laser system of claim 6, wherein the top lenticular incision is moved over the top surface of the lens through an apex of the top surface of the lens, and the bottom lenticular incision is moved over the bottom surface of the lens through an apex of bottom surface of the lens.

8. A method for creating a lenticular incision using an ophthalmic surgical laser system, the method comprising the steps of:
   generating a pulsed laser beam;

delivering the pulsed laser beam to a target in a subject's eye;

deflecting, by an XY-scan device, the pulsed laser beam;

modifying, by a Z-scan device, a depth of a focus of the pulsed laser beam; and controlling, by a controller, the XY-scan device and the Z-scan device to form a top lenticular incision and a bottom lenticular incision of a lens in a cornea of the subject's eye, wherein the top lenticular incision has a top spherical portion at a center and a top edge transition portion that surrounds the top spherical portion, the top spherical portion being a part of a first sphere, the top edge transition portion being not a part of the first sphere and being located within a volume defined by the first sphere, the top lenticular incision being a smooth surface, wherein the bottom lenticular incision has a bottom spherical portion at a center and a bottom edge transition portion that surrounds the bottom spherical portion, the bottom spherical portion being a part of a second sphere, the bottom edge transition portion being not a part of the second sphere and being located within a volume defined by the second sphere, the bottom lenticular incision being a smooth surface, wherein the top and bottom edge transition portions are mirror symmetrical to each other with respect to a transverse center plane perpendicular to an optical axis of the eye, and wherein the top and bottom edge transition portions intersect each other at an intersection location and both extend beyond the intersection location such that the overall lenticule is sufficiently thick to be extracted as a whole piece and the lenticule edge is sufficiently thick to reduce the likelihood of it being torn during extraction.

9. The method of claim 8, wherein in a side cross-sectional view, the top edge transition portion is a part of an ellipse, and the bottom edge transition portion is a part of another ellipse.

10. The method of claim 9, wherein the XY-scan device deflects the pulsed laser beam to form a scan line.

11. The method of claim 10, wherein the scan line is tangential to the parallels of latitude of the lens, the parallels of latitude being circles on the top or bottom lenticular surface that are perpendicular to and center at the optical axis.

12. The method of claim 11, wherein the scan line is moved along the meridians of longitude of the lens, the meridians of longitude being curves formed by an intersection of the top or bottom lenticular surface with side cut planes that pass through the optical axis.

13. The method of claim 12, wherein the top lenticular incision is moved over the top surface of the lens through an apex of the top surface of the lens, and the bottom lenticular incision is moved over the bottom surface of the lens through an apex of bottom surface of the lens.

* * * * *